US009689876B2

(12) United States Patent
Krogsgaard et al.

(10) Patent No.: US 9,689,876 B2
(45) Date of Patent: Jun. 27, 2017

(54) METHODS RELATED TO CANCER TREATMENT

(71) Applicant: NEW YORK UNIVERSITY, New York, NY (US)

(72) Inventors: Michelle Krogsgaard, New York, NY (US); Iman Osman, Jersey City, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/398,377

(22) PCT Filed: May 1, 2013

(86) PCT No.: PCT/US2013/039022
§ 371 (c)(1),
(2) Date: Oct. 31, 2014

(87) PCT Pub. No.: WO2013/166118
PCT Pub. Date: Nov. 7, 2013

(65) Prior Publication Data
US 2015/0125466 A1    May 7, 2015

Related U.S. Application Data

(60) Provisional application No. 61/641,730, filed on May 2, 2012.

(51) Int. Cl.
*G01N 33/573*  (2006.01)
*A61K 39/00*  (2006.01)
*G01N 33/574*  (2006.01)

(52) U.S. Cl.
CPC . *G01N 33/57496* (2013.01); *G01N 33/57407* (2013.01); *G01N 2333/96494* (2013.01); *G01N 2800/52* (2013.01)

(58) Field of Classification Search
None
See application file for complete search history.

(56) References Cited

U.S. PATENT DOCUMENTS

2006/0019914 A1   1/2006  Pourmotabbed et al.

OTHER PUBLICATIONS

Krogsgaard et al J Clin Oncol 29, suppl: abs 8541. Jun. 3-7, 2011, IDS item 5, Oct. 31, 2014, abstract.*
Overall et al, Nature Rev 2:657-672, 2002.*
Chandra et al., "TILs in Metastatic Melanoma Tumors: A Biomarker for Immunotherapy?," Abstract 8589, General Poster Session, Chicago, Illinois, Jun. 1-Jun. 5, 2012, Proceedings of ASCO 2012 Annual Meeting, J Clin Oncol 30 (suppl; abstr 8589) (2012).
Mason et al., "Comparative Study of Matrix Metalloproteinase Expression Between African American and Caucasian Women," J. Carcinogenesis 3(15):1-6 (2004).
Rangaraju et al., "Potassium Channel Modulation by a Toxin Domain in Matrix Metalloprotease 23," J. Biol. Chem. 285(12):9124-9136 (2010).
Velasco et al., "Cloning and Characterization of Human MMP-23, a New Matrix Metalloproteinase Predominantly Expressed in Reproductive Tissues and Lacking Conserved Domains in Other Family Members," J. Biol. Chem. 274(8):4570-4576 (1999).
Nguyen et al., "Intracellular Trafficking of the KV1.3 Potassium Channel Is Regulated by the Prodomain of a Matrix Metalloprotease," J Biol Chem. 288(9): 6451-6464 (e-pub Jan. 8, 2013).
Krogsgaard et al., "An Analysis of Altered Melanoma Matrix Metalloproteinase-23 (Mmp-23) Expression Correlates and Response to Immune Biologic Therapy," Abstract 8541, General Poster Session, 2011 ASCO Annual Meeting, Chicago, Illinois, Jun. 3-7, 2011, J Clin Oncol 29 (suppl; abstr 8541) (2011).
Abgent, "MMP23 Antibody (N-term) Blocking Peptide," www.abgent.com/products/BP6204a_MMP23_Antibody_N_term_Blocking_Peptide (retreived Oct. 5, 2011).

* cited by examiner

*Primary Examiner* — Lei Yao
(74) *Attorney, Agent, or Firm* — LeClairRyan, a Professional Corporation

(57) ABSTRACT

The present invention relates to method for predicting a subject's relative response to cancer immunotherapy treatment. The methods involve providing a sample comprising a tumor cell or a peripheral blood cell from the subject; measuring the expression level of matrix metalloproteinase-23 ("MMP-23") by the tumor cell or the peripheral blood cell; comprising the measured expression level of MMP-23 with a control or standard value; and determining the subject's predicted response to cancer immunotherapy, where, based on said comparing, a higher MMP-23 expression level compared to the control or standard value predicts the subject will have a poor response to cancer immunotherapy. The present invention also relates to methods for increasing production of tumor infiltrating leucocytes ("TILs") in a subject, methods of identifying a subject as a candidate for adoptive T-cell therapy using T-cells that primarily express KCa3.1 channels, and methods of treating a subject having melanoma by administering an MMP-23 inhibitor.

3 Claims, 9 Drawing Sheets

Demographic and clinicopathologic characteristics of patients with recurrent melanomas evaluated for MMP-23 expression

| Patient ID | Age[a] / Gender | Stage at Recurrent Tissue Acquisition | Recurrent MMP-23 Composite Score | Site of First Recurrence | Immunotherapy Received at First Recurrence | Status at Last Follow-Up |
|---|---|---|---|---|---|---|
| 03-088 | 47 F | III | 0 | LR | Biologic | Died, with melanoma |
| 03-178 | 48 F | III | 2 | RLN | Biologic | Died, with melanoma |
| 04-127 | 31 F | III | 0 | RLN | Anti-CTLA-4 | Died, with melanoma |
| 04-168 | 26 F | III | 0 | RLN | Anti-CTLA-4 | Alive, no melanoma |
| 05-055 | 31 M | III | 4 | RS | Anti-CTLA-4 | Died, with melanoma |
| 05-095 | 42 F | III | 0 | RLN | Anti-CTLA-4 | Alive, no melanoma |
| 05-105 | 62 M | III | 0 | RLN | Biologic | Alive, no melanoma |
| 06-098 | 46 M | III | 3 | RLN | Vaccine | Alive, no melanoma |
| 07-014 | 45 F | III | 3 | RS | Biologic | Alive, no melanoma |
| 07-080 | 61 F | III | 3 | RS | Biologic | Alive, with melanoma |
| 07-128 | 35 M | IV | 3 | DV | Anti-CTLA-4 | Died, with melanoma |
| 07-157 | 71 M | IV | 3 | RLN, DV | Biologic | Died, with melanoma |
| 07-163 | 52 M | III | 0 | RS | Vaccine | Alive, no melanoma |
| 07-255 | 42 F | IV | 0 | RS, DS | Anti-CTLA-4 | Died, with melanoma |
| 08-022 | 56 F | IV | 0 | DS | Anti-CTLA-4 | Died, with melanoma |
| 08-140 | 32 F | III | 0 | RLN | Biologic | Died, with melanoma |
| 08-176 | 68 F | IV | 2 | RS, RLN, DV | Biologic | Died, with melanoma |

Abbreviations: LR, local recurrence; RLN, regional lymph node; RS, regional skin; DV, distant visceral; DS, distant skin

[a] Age at initial melanoma diagnosis

*FIG. 1*

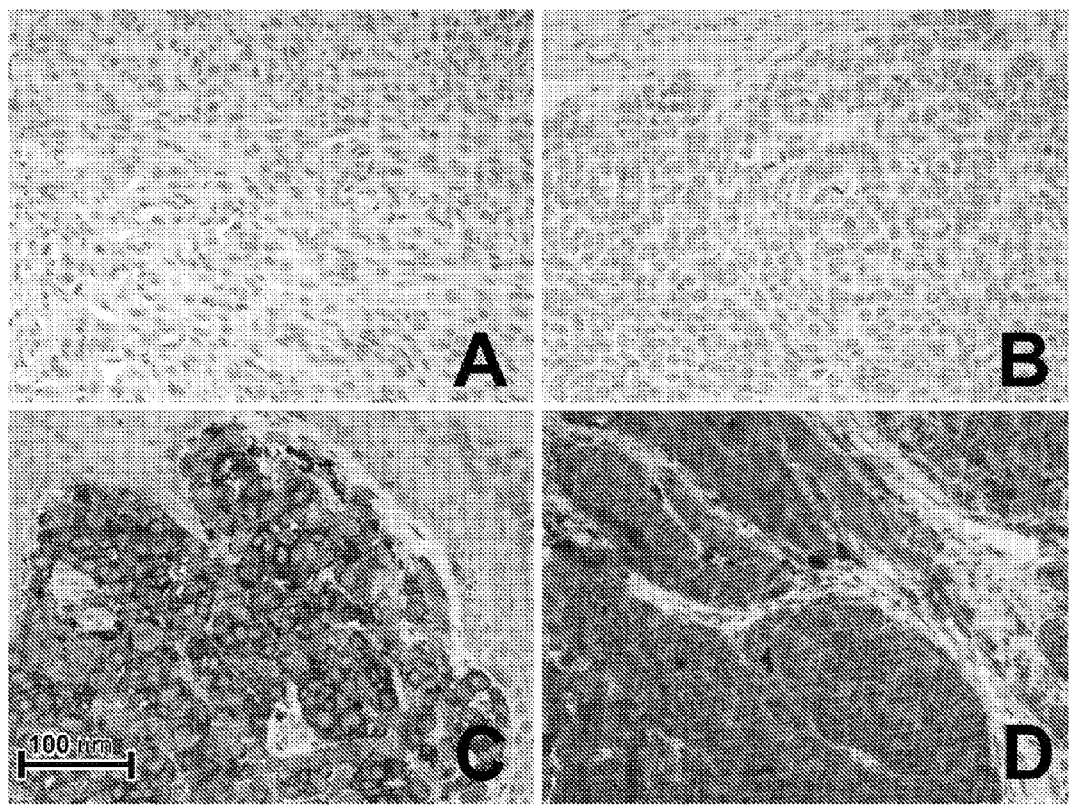
*FIGs. 2A-D*

| Variable | Immunotherapy (n=85) |
|---|---|
| Age at diagnosis (years) | |
| Median (Range) | 55 (21-80) |
| Gender | |
| Male | 50 (58.8%) |
| Female | 35 (41.2%) |
| AJCC stage at diagnosis | |
| I | 20 (23.5%) |
| II | 21 (24.7%) |
| III | 44 (51.8%) |
| Primary TILs | |
| Absent | 20 (23.5%) |
| Present | 62 (72.9%) |
| Non-brisk | 33 |
| Brisk | 28 |
| Present NOS | 1 |
| Unclassified | 3 (3.5%) |
| Type of immunotherapy* | |
| Immune biologic | 41 (48.0%) |
| IFN-α | 22 |
| IL-2 | 4 |
| GM-CSF | 14 |
| Other | 1 |
| Vaccine | 34 (37.4%) |
| Dendritic cell | 12 |
| Peptide | 22 |
| Anti-CTLA-4 antibody | 16 (17.6%) |
| Ipilimumab | 8 |
| Ticilimumab | 8 |
| Type of immunotherapy* | |
| Adjuvent | 43 (47.3%) |
| At Recurrence | 48 (52.7%) |

*Pts who received immunotherapy in both settings (n=6)

FIG. 3

| | MMP-23 Composite Score | | | |
|---|---|---|---|---|
| | Immune biologics[a] | | Vaccines[b] | |
| | 0 - 2 | 3 - 4 | 0 - 2 | 3 - 4 |
| Recurrence | | | | |
| Yes | 0 (0%) | 13 (87%) | 5 (63%) | 10 (71%) |
| No | 4 (100%) | 2 (13%) | 3 (37%) | 4 (29%) |
| Total | 4 (100%) | 15 (100%) | 8 (100%) | 14 (100%) |

| | MMP Score | baseline CD69 | | | | in vitro CD69 upregulation | | | |
|---|---|---|---|---|---|---|---|---|---|
| | | CD4$^+$CCR7$^-$ | CD4$^+$CCR7$^+$ | CD8$^+$CCR7$^-$ | CD8$^+$CCR7$^+$ | CD4$^+$CCR7$^-$ | CD4$^+$CCR7$^+$ | CD8$^+$CCR7$^-$ | CD8$^+$CCR7$^+$ |
| 10-248[a] | 2 | 3.1 | 0.5 | 7.2 | 0.9 | 3.5 | 6.3 | 2.1 | 3.9 |
| 12-019[a] | 2 | 21.8 | 12.5 | 41.2 | 11.2 | N/A[b] | 2.8 | 1.8 | 3.1 |
| 12-126[c] | 2 | 16.5 | 6.1 | 56.4 | 9.6 | 0.2 | 14.9 | 0.4 | 2.4 |
| 09-213-1A[d] | 2 | 1.0 | 0.1 | 1.0 | 0.1 | n/a[b] | n/a[b] | n/a[b] | n/a[b] |
| 10-017[d] | 3 | 14.6 | 1.5 | 12.4 | 1.6 | 3.5 | 46.5 | 3.7 | 24.1 |
| 12-049[e] | 3 | 6.4 | 9.4 | 0.8 | 0.3 | 5.4 | 4.0 | 3.6 | 2.7 |
| 12-126[c] | 3 | 15.0 | 7.1 | 33.6 | 8.4 | 3.2 | 13.9 | 0.9 | 38.9 |

[a] Fresh tissue specimen collected at first recurrence.

[b] Data not available due to poor staining or absence of CD4$^+$CCR7 population.

[c] Fresh tissue specimens were obtained from two distinct lymph nodes at initial melanoma diagnosis.

[d] Fresh tissue specimen collected at subsequent recurrence, not first recurrence.

[e] Fresh tissue specimen collected at initial melanoma diagnosis.

B

| | MMP-23 score | Average | | | |
|---|---|---|---|---|---|
| | | CD4+ CCR7- | CD4+ CCR7- | CD8+ CCR7- | CD8- CCR7+ |
| baseline CD69 | 2 | 10.6 | 4.8 | 26.5 | 5.4 |
| | 3 | 12.0 | 6.0 | 15.6 | 3.5 |
| upregulation CD69 | 2 | 1.9 | 8.0 | 1.4 | 3.1 |
| | 3 | 4.1 | 21.5 | 2.8 | 21.9 |

*FIGs. 8A-B*

METHODS RELATED TO CANCER TREATMENT

This application is a national stage application under 35 U.S.C. 371 from PCT Application No. PCT/US2013/039022, filed May 1, 2013, which claims the benefit of U.S. Provisional Patent Application Ser. No. 61/641,730, filed May 2, 2012, each of which is hereby incorporated by reference in its entirety.

This invention was made with government support under grant number 1U01CA137070 awarded by the National Institutes of Health. The government has certain rights in this invention.

FIELD OF THE INVENTION

The present invention relates to cancer treatment methods and the role of MMP23 as a therapeutic checkpoint.

BACKGROUND OF THE INVENTION

Melanoma is a highly immunogenic tumor (Alexandrescu et al., "Immunotherapy for Melanoma: Current Status and Perspectives," *J. Immunother.* 33(6):570-90 (2010)), yet tumor progression nevertheless occurs in immunocompetent patients. Escape of tumor from immune-mediated destruction can result from tumor release of soluble factors that redirect the immune response, or through mechanisms that limit or inhibit infiltration or function of tumor-infiltrating lymphocytes ("TILs") (Loose & Van de Wiele, "The Immune System and Cancer," *Cancer Biother. Radiopharm.* 24(3):369-76 (2009); Frey & Monu, "Signaling Defects in Anti-Tumor T Cells," *Immunol. Rev.* 222:192-205 (2008); Alexandrescu et al., "Immunotherapy for Melanoma: Current Status and Perspectives," *J. Immunother.* 33(6):570-90 (2010)). Therefore, a number of treatment strategies aim to augment anti-tumor immunity by targeting immunosuppressive mechanisms, including cytotoxic T lymphocyte-associated antigen 4 (CTLA4) and programmed cell death receptor (PD1), thereby unrestraining existing tumor infiltrating lymphocytes (TIL) (Alexandrescu et al., "Immunotherapy for Melanoma: Current Status and Perspectives," *J. Immunother.* 33(6):570-90 (2010)).

Despite the promise of these strategies in combination with existing therapies, and while select subsets of patients do respond strongly to immune-based therapies, because of the morbidity often associated with immunotherapeutics, clinicopathological criteria are sought to better identify those patients who will benefit from specific treatments and to select the optimal immunotherapeutic strategy.

Insights into identifying potential immunotherapeutic responders and novel immune targets in melanoma may be gained from treatment strategies in chronic inflammatory conditions, given the link between cancer and inflammation (Coussens & Werb, "Inflammation and Cancer," *Nature* 420:860-7 (2002)). Anti-inflammatory agents suppress Th1 immunity which is needed for an effective anti-tumor response. Studies in multiple sclerosis and rheumatoid arthritis have shown that the sea anemone peptide ShK diminishes Th1 immunity by selectively blocking the voltage-gated potassium channel Kv1.3 on effector memory T-cells (Tem) (Beeton et al., "Kv1.3 Channels Are a Therapeutic Target for T Cell-Mediated Autoimmune Diseases," *Proc. Nat'l. Acad. Sci. U.S.A.* 103:17414-9 (2006); Rangaraju et al., "Kv1.3 Potassium Channels as a Therapeutic Target in Multiple Sclerosis," *Expert Opin. Ther. Targets* 13:909-24 (2009)). Kv1.3 blocking prevents the efflux of intracellular potassium, thereby diminishing the driving force for sustained calcium influx that is required for robust T-cell proliferation, cytokine production, and motility (Feske, "Calcium Signalling in Lymphocyte Activation and Disease," *Nat. Rev. Immunol.* 7:690-702 (2007); Matheu et al., "Imaging of Effector Memory T Cells During a Delayed-Type Hypersensitivity Reaction and Suppression by Kv1.3 Channel Block," *Immunity* 29(4):602-14 (2008); Cahalan & Chandy, "The Functional Network of Ion Channels in T Lymphocytes," *Immunol. Rev.* 231(1):59-87 (2009)). Matrix metalloproteinase ("MMP")-23, a unique member of the MMP family characterized by its cysteine-rich toxin and immunoglobulin-like domains, contains a toxin domain, MMP-23(TxD), that is structurally similar to ShK, which also selectively blocks Kv1.3 channels (Rangaraju et al., "Potassium Channel Modulation by a Toxin Domain in Matrix Metalloprotease 23," *J. Biol. Chem.* 285:9124-36 (2010)). The focus on tumor-derived MMPs in melanoma and other cancers, including breast, prostate, lung, and colon cancer, has been their ability to mediate microenvironmental changes regulating cancer progression, including the break down of extracellular matrix and promotion of growth/neoangiogenesis (Hofmann et al., "Matrix Metalloproteinases in Human Melanoma," *J. Invest. Dermatol.* 115:337-44 (2000); Egeblad & Werb, "New Functions for the Matrix Metalloproteinases in Cancer Progression," *Nat. Rev. Cancer* 2:161-74 (2002); Roy et al., "Matrix Metalloproteinases as Novel Biomarkers and Potential Therapeutic Targets in Human Cancer," *J. Clin. Oncol.* 27:5287-97 (2009)). Further, a recent study by Bhardwaj and colleagues demonstrated a role for MMPs in influencing T-cell phenotype by showing that active MMP-2 induces Th2 skewing by blocking IL-12 and inducing OX40L on DCs (Godefroy et al., "Matrix Metalloproteinase-2 Conditions Human Dendritic Cells to Prime Inflammatory $T(H)_2$ Cells Via an IL-12- and OX40L-Dependent Pathway," *Cancer Cell* 19(3):333-46 (2011)). However, in general, the role of tumor-derived MMPs in the induction of immune escape has been less explored.

The present invention is directed to overcoming these and other deficiencies in the art.

SUMMARY OF THE INVENTION

One aspect of the present invention relates to a method for predicting a subject's relative response to cancer immunotherapy treatment. This method comprises providing a sample comprising a tumor cell or a peripheral blood cell from the subject; measuring the expression level of matrix metalloproteinase-23 (MMP-23) by the tumor cell or the peripheral blood cell in the sample; comparing the measured expression level of MMP-23 with a control or standard value; and determining the subject's predicted response to cancer immunotherapy, where, based on said comparing, a higher MMP-23 expression level compared to the control or standard value predicts the subject will have a poor response to cancer immunotherapy.

Another aspect of the present invention relates to a method for increasing production of tumor infiltrating leucocytes (TILs) in a subject. This method comprises selecting a subject in need of increased production of TILs and administering an MMP-23 inhibitor to the subject under conditions effective to increase production of TILs in the subject.

Yet another aspect of the present invention relates to a method of identifying a subject as a candidate for adoptive T-cell therapy using T-cells that primarily express KCa3.1 channels. This method comprises providing a tumor cell from a subject with a tumor; measuring the expression level of MMP-23 by the tumor cell; comparing, based on the measuring, the expression level of MMP-23 with a control or standard value; and identifying the subject as a candidate for adoptive T-cell therapy using T-cells that primarily express KCa3.1 channels, wherein, based on said comparing, the tumor cell has a higher MMP-23 expression level compared to the control or standard value.

Yet a further aspect of the present invention relates to a method of treating a subject for melanoma. This method comprises selecting a subject having melanoma and administering an MMP-23 inhibitor to the subject under conditions effective to treat melanoma in the subject.

The present invention characterizes, for the first time, MMP-23 expression in human melanoma as it relates to intrinsic anti-tumor immune response, the systemic anti-tumor immune response, and response to immunotherapy. The data set forth in the Examples demonstrate a role for MMP-23 overexpression in blunted intrinsic anti-tumor response, as well as response to specific categories of immunotherapy.

BRIEF DESCRIPTION OF THE DRAWINGS

FIG. 1 is a table setting forth demographic and clinicopathologic characteristics of patients with recurrent melanomas evaluated for MMP-23 expression.

FIGS. 2A-D are photographs showing representative melanoma MMP-23 immunohistochemical scoring. Composite score=0 (FIG. 2A); Composite score=3 (intensity=1, distribution=2) with faint cytoplasmic immunopositivity (FIG. 2B); Composite score=4 (intensity=2, distribution=2) with intense cytoplasmic reactivity (FIG. 2C); Composite score=5 (intensity=3, distribution=2) with very intense cytoplasmic reactivity (400×) (FIG. 2D).

FIG. 3 is a table setting forth demographic and clinicopathologic characterstics of melanoma patients treated with immunotherapy.

FIG. 4 is a table showing the results of stratified analysis of melanoma recurrence risk by type of adjuvant immunotherapy: immune biologics and vaccines. Immune biologics included INF-α and GM-CSF, and vaccines.

FIGS. 6C and 6D show corresponding consecutive MMP23 staining of sections (FIG. 6A) and (FIG. 6B) respectively.

In FIG. 7A, CD69 expression is higher in samples from patients with lower MMP-23 expression. In FIG. 7B, upon in vivo activation, Tem from patients with higher MMP-23 expression showed greater CD69 upregulation.

FIGS. 8A-B are tables setting forth T cell CD69 expression results in fresh tissue specimens of melanoma patients.

DETAILED DESCRIPTION OF THE INVENTION

Figures 5A, 5B, 5C, 5D:
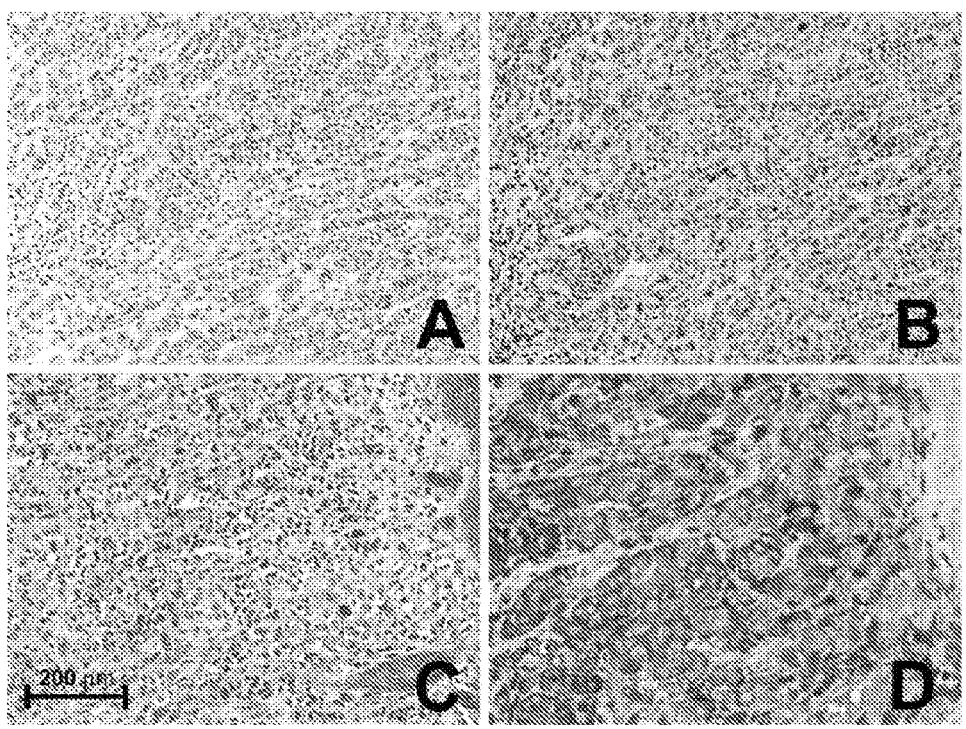
FIGS. 5A-D are photographs showing that the intensity of lymphocytic infiltration decreases with increased melanoma MMP-23 expression. Hematoxylin-and-eosin-stained primary melanoma specimens showing a representative brisk (FIG. 5A) and absent (FIG. 5C) lymphocytic infiltrate and the corresponding consecutive MMP-23-stained sections (FIG. 5B and FIG. 5D, respectively) with MMP-23 composite scores of 2 and 4, respectively (80×).
Figures 6A, 6B, 6C, 6D:
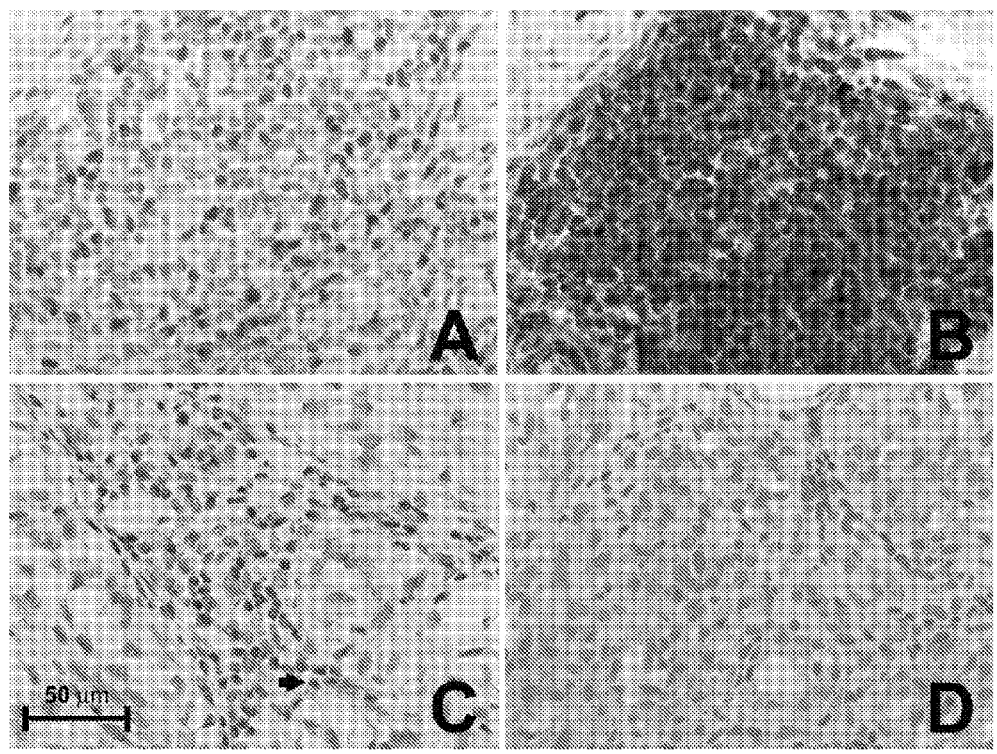
FIGS. 6A-D are photographs showing that Foxp3+ $T_{regs}$ in the primary tumor increases with higher melanoma MMP-23 expression. Heterogeneous nuclear positivity for Foxp3 in TILs from a primary melanoma with a high MMP-23 composite score and 100 Foxp3+ $T_{regs}$/high-power field (FIG. 6A). Nuclear reactivity for Foxp3 limited to a few TILs (5 Foxp3+ $T_{regs}$/high-power field) (arrowheads) from a primary melanoma with no MMP-23 expression (200×) (FIG. 6B).

One aspect of the present invention relates to a method for predicting a subject's relative response to cancer immunotherapy treatment. This method comprises providing a sample comprising a tumor cell or a peripheral blood cell from the subject; measuring the expression level of matrix metalloproteinase-23 (MMP-23) by the tumor cell or the peripheral blood cell in the sample; comparing the measured expression level of MMP-23 with a control or standard value; and determining the subject's predicted response to cancer immunotherapy, where, based on said comparing, a higher MMP-23 expression level compared to the control or standard value predicts the subject will have a poor response to cancer immunotherapy.

In carrying out this method of the present invention, a subject's relative response to cancer immunotherapy treatment is, according to one embodiment, a response based on a scale of response that, on one end of the spectrum is a complete response to treatment and on the other end of the spectrum is a poor response to treatment (e.g., stable or progressive disease responses). In one embodiment, this response is evaluated using the Response Evaluation Criteria in Solid Tumors ("RECIST"), version 1.1 (Eisenhauer et al., "New Response Evaluation Criteria in Solid Tumours: Revised RECIST Guideline (version 1.1)," *European J. Cancer* 45:228-247 (2009), which is hereby incorporated by reference in its entirety). Thus, in carrying out this method, a poor response to immunotherapy includes a progressive disease response or stable disease response as categorized using RECIST.

In one embodiment, measuring the expression level of MMP-23 according to the present invention includes contacting the sample or tumor cell with a reagent suitable for detecting the level of MMP-23 expression in the sample and measuring the expression level of MMP-23 in the sample or by the tumor cell based on the contacting.

Measuring the expression level of MMP-23 by a cell in accordance with the present invention can be achieved by methods known to those of ordinary skill in the art. In one embodiment, MMP-23 protein expression is assessed in a tumor cell or tissue obtained from the subject. The level of MMP-23 protein expression in this sample is compared to the level of MMP-23 protein expression in a normal tissue obtained from a subject. An expression level of MMP-23 that is higher in the tumor cell(s) sample compared to the normal tissue indicates or predicts that the subject will have a poor response to cancer immunotherapy. For example, MMP-23 expression can be evaluated by immunohistochemical analysis of a sample. For example, MMP-23 expression can be measured by providing an anti-MMP-23 antibody, contacting the antibody with a sample, visualising or detecting any antibody-MMP-23 reaction. The detecting or visualizing can be accomplished in a number of ways (e.g., an antibody is conjugated to a compound (e.g., an enzyme, such as peroxidase) that is capable of producing color upon reaction. Alternatively, the antibody can also be tagged to a fluorophore. The sample can then be scored for staining intensity (e.g., 0=none, 1=faint, 2=intense, 3=very intense) and distribution (e.g., 0=none, 1=faint (<50%), 2=diffuse (>50%)). These scores can be summed to generate a composite score for each sample. In one embodiment, a high composite score is 3-4, compared to a normal tissue with a composite score of 0-2, predicts that the subject will have a poor response to cancer immunotherapy.

The expression level of MMP-23 in a control or standard value may be that associated with a sample from tumor tissue obtained from a subject that has undergone successful cancer immunotherapy (e.g., complete or partial remission). Such a control or standard value may also be based on a known reference value of MMP-23 expression. It should be noted that expression can be measured according to any convenient method.

Sample protein from the subject can be isolated and prepared from tissue or cells using standard preparation methods known in the art. For example, tissue and cells can be lysed in buffer containing a detergent, such as sodium dodecyl sulfate ("SDS"), and a cocktail of protease inhibitors. Protein yield can be determined using the Bradford Assay or any variation of the method known in the art. Assessing the level of expression of a target protein within a sample can be performed by various techniques known in the art. For example, assessing the level of expression can involve analyzing one or more proteins by two-dimensional gel electrophoresis, mass spectroscopy, high performance liquid chromatography ("HPLC"), fast protein liquid chromatography, multi-dimensional liquid chromatography followed by tandem mass spectrometry, or protein chip expression analysis. As noted above, other techniques, using antibodies or other agents which selectively bind to the protein of interest, commonly used for assessing protein expression include Western Blot, immunoprecipitation, enzyme-linked immunosorbent assay ("ELISA"), radioimmunoassay ("RIA"), or fluorescent activated cell sorting ("FACS"). Immunohistochemical and immunofluorescent techniques in which antibody binding to specific protein target is visualized within a whole cell or whole tissue sample is also contemplated.

In another embodiment of the present invention, MMP-23 gene expression level is measured. For example, MMP-23 mRNA expression is assessed in a tumor cell, such as a melanoma tumor cell, obtained from the subject. The level of MMP-23 mRNA expression in this sample is compared to the level of MMP-23 mRNA expression in a normal tissue obtained from a subject. An expression level of MMP-23 mRNA that is higher in the tumor cell(s) sample compared to the normal tissue indicates or predicts that the subject will have a poor response to cancer immunotherapy.

Sample RNA from the subject can be isolated and prepared from tissue or cells using methods known in the art. The RNA preparation must produce enzymatically manipulatable mRNA or analyzable RNA. The RNA may be isolated using the guanidinium isothiocyanate-ultracentrifugation method, the guanidinium and phenol-chloroform method, the lithium chloride-SDS urea method, or the poly A+/mRNA from tissue lysates using oligo (dT) cellulose method. It is important that the quality and quantity of the RNA yield is assessed prior to quantitative gene expression analysis. Total isolated RNA can be used to generate first strand copy DNA (cDNA) using any known procedure in the art, for example, using random primers, oligo-dT primers, or random-oligo-dT primers. The cDNA can then be used as a template for a first round amplification reaction or for the quantitative PCR reaction depending on target or sample abundance. The first round PCR amplification is performed with a primer set, including forward and reverse primers, that are specific for the target gene of interest. Following the first round of amplification, a cleaned portion of the reaction product is used for quantitative analysis. Quantitative real-time PCR protocols typically rely on fluorescent detection of product formation following the extension phase of the reaction cycle. Typical fluorescent approaches for quantitative PCR are based on fluorescent reporter dyes such as SYBR green, FAM, fluorescein, HEX, TET, TAMRA, etc. and quencher dyes such as DABSYL, Black Hole, etc. Systems, such as Molecular Beacons (Integrated DNA Technologies, Coralville, Iowa), Taqman Probes® (Applied Biosystems, Foster City, Calif.), or Scorpion® Primers (DxS Ltd., Manchester, UK), are also well known in the art of quantitative gene analysis. Examples of methods and reagents related to real time probes can be found in U.S. Pat. Nos. 5,925,517; 6,103,476; 6,150,097; and 6,037,130 all to Tyagi et al., which are hereby incorporated by reference in their entirety.

Quantitative gene expression can be expressed as absolute copy number or as relative gene expression. Both methods utilize a standard curve from which to accurately obtain quantitative data. Alternatively, relative gene expression can also be calculated using the Comparative $C_T$ Method as described in the ABI Prism 7700 Sequence Detection System User Bulletin #2, which is hereby incorporated by reference in its entirety. The Comparative $C_T$ method is similar to the standard curve method, except it uses an arithmetic formula to calculate the relative gene expression data. A detailed description of absolute and relative gene expression quantitation is provided in the ABI Prism 7700 Sequence Detection System User Bulletin #2, which is hereby incorporated by reference in its entirety. A preferable embodiment of this aspect of the invention is the analysis of MMP-23 gene expression in tumor cells.

Accordingly, reagents suitable for contacting with a sample to detect MMP-23 includes a reagent capable of reacting with or binding to MMP-23 or MMP-23 mRNA. For example, such reagents include, but are not limited to, a liquid chromatography reagent, an antibody, a peptide capable of reacting with (e.g., binding to) MMP-23, a ligand, a drug, a fluorphore, a peptide aptamer, a DNA molecule, an RNA molecule, and the like. In one embodiment, the reagent comprises an antibody.

The gene expression level of MMP-23 in a control or standard value may be that associated with a sample from tumor tissue obtained from a subject that has undergone successful cancer immunotherapy (e.g., complete or partial remission). Such a control or standard value may also be based on a known reference value of MMP-23 gene expression. As noted above, expression can be measured according to any convenient method.

In one embodiment, the subject is predicted to have a poor response to immunotherapy. The prediction of poor response to immunotherapy may also predict a greater cancer recurrence rate if the subject is treated with a cancer immunotherapy. Cancer recurrence is a return of the particular cancer after a period of time in which no cancer could be detected.

In another embodiment, the prediction of poor response to immunotherapy also predicts a greater cancer recurrence rate if the subject is treated with a cancer immunotherapy that is an immune biologic. Suitable immune biologics include, without limitation, interferon-alpha and GM-CSF.

In a further embodiment, the method further comprises assigning a course of treatment based on the predicted response to immunotherapy and/or carrying out or administering a course of treatment.

In yet another embodiment, the subject is predicted to have a poor response to immunotherapy and the course of treatment assigned includes administering an MMP-23 inhibitor. Suitable MMP-23 inhibitors are described herein. In one embodiment the course of treatment includes administering an MMP-23 inhibitor in conjunction with an anti-cancer agent, an anti-metastatic agent, or combinations thereof. Exemplary anti-cancer and anti-metastatic agents are described herein. The MMP-23 inhibitor may be administered prior to, during, and/or after the course of the treatment with anti-cancer agent, or an anti-metastatic agent, or in combination.

In yet a further embodiment, the course of treatment involves administering a cancer therapeutic other than an immunotherapy.

In another embodiment, the assigned course of treatment includes adoptive T-cell therapy using T cells that primarily express KCa3.1 channels.

Suitable tumor cells in accordance with the present invention include tumor cells associated with any cancer mediated by overexpression of MMP-23, including a tumor cell associated with skin cancer, breast cancer, prostate cancer, lung cancer, and/or colon cancer. In one embodiment, the tumor cell is associated with melanoma.

Suitable samples for use in accordance with the present invention that comprise such tumor cells and/or peripheral blood cells are from a subject having any of the above-mentioned cancers. In one embodiment, a sample comprising a tumor cell and/or a peripheral blood cell is provided from a subject having melanoma. Suitable samples include any suitable biological sample. More particularly, the invention provides assays for the detection of MMP-23 in a biological sample, such as serum, bone, and other tissues, cell preparations, and the like. Peripheral blood may be conveniently assayed for the presence of MMP-23 and/or cells expressing MMP-23. Accordingly, in one embodiment, the sample is a peripheral blood sample. In another embodiment, the sample is a primary tumor tissue sample.

Suitable subjects in accordance with the present invention include mammals. In one preferred embodiment, the subject is a human.

In one embodiment, the method according to the present invention further includes measuring tumor infiltrating leucocytes (TILs) present in the sample, comparing the level of TILs present in the sample with a control or standard value, and determining the subject's predicted response to cancer immunotherapy. In this embodiment, based on said comparing, a higher MMP-23 expression level, compared to the control or standard value, and a lower level of TILs, compared to the control or standard value, predicts the subject will have a poor response to cancer immunotherapy. In this embodiment, a higher melanoma MMP-23 expression level, as compared to a standard or control value, is inversely associated with the presence of TILs in a sample.

In one embodiment, the TILs are brisk TILs.

TILs may be classified as absent, non-brisk, and brisk. (Clark et al., "Model Predicting Survival in Stage I Melanoma Based on Tumor Progression," *J. Nat'l Cancer Inst.* 81:1893-1904 (1989), which is hereby incorporated by reference in its entirety). In one embodiment, TILs are defined as brisk when present throughout the vertical growth phase (i.e., large dermal aggregates of melanoma over 15-25 cells wide) or present and infiltrating across the entire base of the vertical growth phase. (Clark et al., "Model Predicting Survival in Stage I Melanoma Based on Tumor Progression," *J. Nat'l Cancer Inst.* 81:1893-1904 (1989), which is hereby incorporated by reference in its entirety).

Another aspect of the present invention relates to a method for increasing production of TILs in a subject. This method involves selecting a subject in need of increased production of TILs and administering an MMP-23 inhibitor to the subject under conditions effective to increase production of TILs in the subject.

In carrying out this method, a subject is selected as described supra. Specifically, in one embodiment, a subject that is predicted to have a poor response to cancer immunotherapy according to the methods described above is selected. The method for predicting a subject's relative response to cancer immunotherapy treatment comprises providing a sample comprising a tumor cell or a peripheral blood cell from the subject; measuring the expression level of MMP-23 by the tumor cell or the peripheral blood cell; comparing, based on the measuring, the expression level of MMP-23 with a control or standard value; and determining the subject's predicted response to cancer immunotherapy, where, based on said comparing, a higher MMP-23 expression level compared to the control or standard value predicts the subject will have a poor response to cancer immunotherapy.

A subject in need of increased production of TILs includes any subject that would benefit from enhanced T-cell mediated response to an antigenic stimulus from a tumor. This also includes a candidate for adoptive T-cell therapy. In one embodiment, the candidate is predicted to have a poor response to such therapy based on the elevated level of MMP-23 expression as compared to a normal or standard value.

In one embodiment according to the present invention, the TILs are part of a brisk TIL response. Classification of TILs is described supra.

Administration of an MMP-23 inhibitor according to the present invention increases the T-cell response to tumor antigen mediated activation. For example, an increase in T-cell response may be measured by an increase in T-cell activity. Useful measures of T-cell activity are proliferation, the release of cytokines (e.g., IL-2, IFNg, TNFa), T cell expression of markers (e.g., CD25 and CD69), and other measures of T cell activity as known in the art.

In accordance with the present invention, the MMP-23 inhibitor includes inhibitors selected from the group consisting of a nucleic acid molecule, an inhibitory polypeptide, an antibody, and a small molecule, each of which is described in more detail below.

Exemplary nucleic acid MMP-23 inhibitors include antisense RNAs or RNAi, such as short interfering RNAs (siRNA), short hairpin RNAs (shRNA), and microRNAs.

The use of antisense methods to inhibit the in vivo translation of genes and subsequent protein expression is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modifications that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, H. M., "Antisense DNA and RNA," *Scientific Am.* 262:40-46 (1990), which is hereby incorporated by reference in its entirety). The antisense nucleic acid molecule hybridizes to its corresponding target nucleic acid molecule, such as the MMP-23 mRNA, to form a double-stranded molecule, which interferes with translation of the mRNA, as the cell will not translate a double-stranded mRNA. Antisense nucleic acids used in the methods of the present invention are typically at least 10-12 nucleotides in length, or at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the MMP-23 nucleotide sequence (GenBank Accession Nos. NM_006983 and XM_001125488, which are hereby incorporated by reference in their entirety). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway.

Nucleic acid aptamers that specifically bind to MMP-23 are also useful in the methods of the present invention. Nucleic acid aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

MMP-23 inhibitors of the present invention also include inhibitory peptides. Suitable inhibitory peptides of the present invention include short peptides based on the sequence of MMP-23 that exhibit inhibition of MMP-23 binding to and direct biological antagonist activity. The amino acid sequence of human MMP-23 from which inhibitory peptides are derived is the amino acid sequence of GenBank Accession Nos. NP_008914 and XP_001125488, which are hereby incorporated by reference in their entirety.

Suitable inhibitory peptides of the present invention include modified MMP-23 peptides that bind, preferably, specifically to the MMP-23 protein but prevent normal MMP-23-T-cell signaling. In a preferred embodiment, the modified MMP-23 peptide has an N-terminal truncation or extension that abrogates its signaling activity while preserving its binding properties. Such inhibitory peptides may be chemically synthesized using known peptide synthesis methodology or may be prepared and purified using recombinant technology. Such peptides are usually at least about 4 amino acids in length, but can be anywhere from 4 to 100 amino acids in length. Such peptides may be identified without undue experimentation using well known techniques. Techniques for screening peptide libraries for peptides that are capable of specifically binding to a polypeptide target, in this case MMP-23, are well known in the art (see e.g., U.S. Pat. No. 5,556,762 to Pinilla et al.; U.S. Pat. No. 5,750,373 to Garrard et al.; U.S. Pat. No. 4,708,871 to Geysen; U.S. Pat. No. 4,833,092 to Geysen; U.S. Pat. No. 5,223,409 to Ladner et al.; U.S. Pat. No. 5,403,484 to Ladner et al.; U.S. Pat. No. 5,571,689 to Heuckeroth et al.; U.S. Pat. No. 5,663,143 to Ley et al.; and PCT Publication Nos. WO84/03506 to Geysen and WO84/03564 to Geysen, which are hereby incorporated by reference in their entirety).

In one embodiment of the present invention, the MMP-23 inhibitor is an antibody. An antibody of the present invention encompasses any immunoglobulin molecule that specifically binds to an epitope of MMP-23. As used herein, "epitope" refers to a region of the MMP-23 protein that is recognized by the isolated antibody and involved in mediating the binding interaction between MMP-23 and T-cells (particularly the interaction between the ShK domain of MMP-23 and the T-cell Kv1.3 channel). In a preferred embodiment, the antibody of the present invention has antigen specificity to the extracellular domain of MMP-23. Suitable MMP-23 antibodies and methods of making the same are known (e.g., those disclosed in Pei et al., "Cysteine Array Matrix Metalloproteinase (CA-MMP)/MMP-23 Is a Type II Transmembrane Matrix Metalloproteinase Regulated by a Single Cleavage for Both Secretion and Activation," J. Biol. Chem. 275(43):33988-97 (2000) (which is hereby incorporated by reference in its entirety), as well as ab74215 and ab39088 (both available from Abcam), the descriptions of which are available from Abcam and which are hereby incorporated by reference in their entirety).

The epitope recognized by the antibody of the present invention may be a linear epitope, i.e. the primary structure of the amino acid sequence of MMP-23. Alternatively, the epitope recognized by the isolated antibody of the present invention is a non-linear or conformational epitope, i.e. the tertiary or quaternary structure of the MMP-23 protein.

As used herein, the term "antibody" is meant to include intact immunoglobulins derived from natural sources or from recombinant sources, as well as immunoreactive portions (i.e. antigen binding portions) of intact immunoglobulins. The antibodies of the present invention may exist in a variety of forms including, for example, polyclonal antibodies, monoclonal antibodies, intracellular antibodies, antibody fragments (e.g. Fv, Fab and F(ab)$_2$), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli,*" *Proc. Natl. Acad. Sci. USA* 85:5879-5883 (1988); Bird et al, "Single-Chain Antigen-Binding Proteins," *Science* 242:423-426 (1988), which are hereby incorporated by reference in their entirety).

In one embodiment, the MMP-23 inhibitor is a human monoclonal antibody or an active binding fragment thereof. Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., an epitope of MMP-23) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur. J. Immunol.* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively, monoclonal antibodies can be made using recombinant DNA methods as described in U.S. Pat. No. 4,816,567 to Cabilly et al., which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate monoclonal antibodies. Alternatively, recombinant monoclonal antibodies or fragments thereof of the desired species can be isolated from phage display libraries (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222: 581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimum to no non-human sequences.

An antibody can be humanized by substituting the complementarity determining region (CDR) of a human antibody with that of a non-human antibody (e.g., mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Human antibodies can be produced using various techniques known in the art. For example, immortalized human B lymphocytes immunized in vitro or isolated from an immunized individual that produce an antibody directed against a target antigen can be generated (see e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, human antibodies can be selected from a phage library that expresses human antibodies (Vaughan et al., "Human Antibodies with Sub-Nanomolar Affinities Isolated from a Large Non-immunized Phage Display Library," *Nature Biotechnology* 14:309-314 (1996); Sheets et al., "Efficient Construction of a Large Nonimmune Phage Antibody Library: The Production of High-Affinity Human Single-Chain Antibodies to Protein Antigens," *Proc. Natl. Acad. Sci. U.S.A.* 95:6157-6162 (1998); Hoogenboom et al., "By-passing Immunisation. Human Antibodies From Synthetic Repertoires of Germline VH Gene Segments Rearranged In Vitro," *J. Mol. Biol.* 227:381-8 (1992); Marks et al., "By-passing Immunization. Human Antibodies from V-gene Libraries Displayed on Phage," *J. Mol. Biol.* 222:581-97 (1991), which are hereby incorporated by reference in their entirety). Human antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety Procedures for raising polyclonal antibodies are also well known. Typically, such antibodies can be raised by administering the peptide or polypeptide containing the epitope of interest subcutaneously to New Zealand white rabbits which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

In addition to whole antibodies, the present invention encompasses binding portions of such antibodies. Such binding portions include the monovalent Fab fragments, Fv fragments (e.g., single-chain antibody, scFv), single variable $V_H$ and $V_L$ domains, and the bivalent $F(ab')_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

The present invention also encompasses the use of bispecific humanized antibodies or bispecific antigen-binding fragments (e.g., $F(ab')_2$) which have specificity for MMP-23 and a molecule expressed on a target cell (e.g., a tumor cell). Techniques for making bispecific antibodies are common in the art (Brennan et al., "Preparation of Bispecific Antibodies by Chemical Recombination of Monoclonal Immunoglobulin G1 Fragments," *Science* 229:81-3 (1985); Suresh et al, "Bispecific Monoclonal Antibodies From Hybrid Hybridomas," *Methods in Enzymol.* 121:210-28 (1986); Traunecker et al., "Bispecific Single Chain Molecules (Janusins) Target Cytotoxic Lymphocytes on HIV Infected Cells," *EMBO J.* 10:3655-3659 (1991); Shalaby et al., "Development of Humanized Bispecific Antibodies Reactive with Cytotoxic Lymphocytes and Tumor Cells Overexpressing the HER2 Protooncogene," *J. Exp. Med.* 175:217-225 (1992); Kostelny et al, "Formation of a Bispecific Antibody by the Use of Leucine Zippers," *J. Immunol.* 148: 1547-1553 (1992); Gruber et al., "Efficient Tumor Cell Lysis Mediated by a Bispecific Single Chain Antibody Expressed in *Escherichia coli,*" *J. Immunol.* 152:5368-74 (1994); and U.S. Pat. No. 5,731,168 to Carter et al., which are hereby incorporated by reference in their entirety). Generally, bispecific antibodies are secreted by triomas (i.e., lymphoma cells fuse to a hybridoma) and hybrid hybridomas. The supernatants of triomas and hybrid hybridomas can be assayed for bispecific antibody production using a suitable assay (e.g., ELISA), and bispecific antibodies can be purified using conventional methods. These antibodies can then be humanized according to methods known in the art. Humanized bispecific antibodies or a bivalent antigen-binding fragment of the bispecific antibody having binding specificity for MMP-23 and an antigen expressed on a target cell, provides a cell-specific targeting approach.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention also encompasses the nucleic acid molecules that encode the MMP-23 antibodies of the invention. The nucleic acids may be present in whole cells, in a cell lysate, or in a partially purified or substantially pure form (i.e., purified away from other cellular components or other contaminants).

Nucleic acids encoding the antibodies of the present invention can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), the nucleic acid encoding the antibody can be recovered from the library.

Preferred nucleic acid molecules of the invention are those encoding the $V_H$ and $V_L$ sequences of MMP-23 monoclonal antibodies. Once DNA or cDNA fragments encoding $V_H$ and $V_L$ segments are obtained, these DNA fragments can be further manipulated by standard recombinant DNA techniques, for example to convert the variable region genes to full-length antibody chain genes, to Fab fragment genes, or to a scFv gene. In these manipulations, a $V_L$- or $V_H$-encoding DNA fragment is operatively linked to another DNA fragment encoding another protein, such as an antibody constant region or a flexible linker The isolated DNA encoding the $V_H$ region can be converted to a full-length heavy chain gene by operatively linking the $V_H$-encoding DNA to another DNA molecule encoding heavy chain constant regions (CH1, CH2, and CH3). The sequences of human heavy chain constant region genes are known in the art (see e.g., Kabat et al., Sequences of Proteins of Immunological Interest, $5^{th}$ ed., U.S. Department of Health and Human Services, NIH Publication No. 91-3242 (1991), which is hereby incorporated by reference in its entirety) and DNA fragments encompassing these regions can be obtained by standard PCR amplification. The heavy chain constant region can be an IgG1, IgG2, IgG3, IgG4, IgA, IgE, IgM, or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region. The sequences of human light chain constant region genes are known in the art (see e.g., Kabat et al., Sequences of Proteins of Immunological Interest, $5^{th}$ ed., U.S. Department of Health and Human Services, NIH Publication No. 91-3242 (1991), which is hereby incorporated by reference in its entirety) and DNA fragments encompassing these regions can be obtained by standard PCR amplification. The light chain constant region can be a kappa or lambda constant region, but most preferably is a kappa constant region.

To create a scFv gene, the $V_H$- and $V_L$-encoding DNA fragments are operatively linked to another fragment encoding a flexible linker such that the $V_H$ and $V_L$ sequences can be expressed as a contiguous single-chain protein, with the $V_H$ and $V_L$ regions joined by the flexible linker (see e.g., Bird et al., "Single Chain Antigen-Binding Proteins," *Science* 242:423-426 (1988); Huston et al., "Protein Engineering of Antibody Binding Sites Recovery of Specific Activity in an Anti-Digoxin Single-Chain Fv Analogue Produced in *Escherichia coli,"Proc. Natl. Acad. Sci. USA* 85:5879-5883 (1988); McCafferty et al., "Phage Antibodies: Filamentous Phage Displaying Antibody Variable Domains," *Nature* 348: 552-554 (1990), which are hereby incorporated by reference in their entirety).

Antibody mimics are also suitable inhibitors for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

In one embodiment, the MMP-23 inhibitor is an inhibitor of furin-mediated cleavage of pro-MMP-23 to active MMP-23 (Coppola et al., "A Small-Molecule Furin Inhibitor Inhibits Cancer Cell Motility and Invasiveness," *Neoplasia* 10(4):363-70 (2008), which is hereby incorporated by reference in its entirety). Such inhibitors may be designed using molecular dynamics simulation.

The MMP-23 inhibitor according to the present invention may also be administered in combination with other therapeutics. The MMP-23 inhibitor may be administered prior to, during, and/or after the other therapeutic. In one embodiment, the MMP-23 inhibitor is administered together with an anti-cancer agent, an anti-metastatic agent, or combinations thereof. In one embodiment, the anti-cancer agent is an immunotherapeutic anti-cancer agent. In one embodiment, the immunotherapeutic anti-cancer agent comprises an immune biologic, vaccine, or anti-CTLA-4 monoclonal antibody. In another embodiment, the immunotherapeutic anti-cancer agent includes a self-antigen selected from the group consisting of tumor cell lysate, dead or dying tumor cells, purified antigen protein, tumor vaccine, tumor infiltrating leukocytes, peripheral blood cells, and combinations thereof. In yet another embodiment, the immunotherapeutic anti-cancer agent comprises an immune biologic selected from the group consisting of interferon-α, interleukin-2, GM-CSF, and combinations thereof.

The MMP-23 inhibitor is administered at a dose effective to increase the response of T cells to antigenic stimulation. The response of activated T cells will be affected by the subject treatment to a greater extent than resting T cells. The determination of the T cell response will vary with the condition that is being treated. Useful measures of T cell activity are proliferation, the release of cytokines, e.g. IL-2, IFNg, TNFa; T cell expression of markers such as CD25 and CD69; and other measures of T cell activity as known in the art.

In accordance with the methods of the present invention, the mode of administering the MMP-23 inhibitor of the present invention, including the use of suitable delivery vehicles, to a subject will vary depending on the type of inhibitor (e.g., nucleic acid molecule, inhibitory peptide, antibody, or small molecule).

In one embodiment, inhibitory MMP-23 nucleic acid molecules (i.e., antisense, siRNA, etc.), nucleic acid molecules encoding a MMP-23 inhibitory peptide, or nucleic acid molecules encoding a MMP-23 antibody or antibody binding fragment may be incorporated into a gene therapy vector to facilitate delivery.

In a preferred embodiment, the gene therapy vector carrying the inhibitory MMP-23 nucleic acid molecule, nucleic acid molecule encoding an inhibitory MMP-23 peptide, or nucleic acid molecule encoding a MMP-23 antibody or antibody binding fragment is an expression vector derived from a virus. Suitable viral vectors include, without limitation, adenovirus, adeno-associated virus, retrovirus, lentivirus, or herpes virus.

Adenoviral viral vector gene delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral gene delivery vehicles can be constructed and used to deliver a gene, including a gene encoding an antibody to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-Associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable In Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver inhibitory nucleic acid molecules or nucleic acid molecules encoding a desired peptide or antibody to a target cell. One such type of retroviral vector is disclosed in U.S. Pat. No. 5,849,586 to Kriegler et al., which is hereby incorporated by reference in its entirety.

Gene therapy vectors carrying the therapeutic nucleic acid molecule are administered to a subject by, for example, intravenous injection, local administration (U.S. Pat. No. 5,328,470 to Nabel et al., which is hereby incorporated by reference in its entirety) or by stereotactic injection (see e.g., Chen et al. "Gene Therapy for Brain Tumors: Regression of Experimental Gliomas by Adenovirus Mediated Gene Transfer In Vivo," *Proc. Nat'l. Acad. Sci. USA* 91:3054-3057 (1994), which is hereby incorporated by reference in its entirety). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. Gene therapy vectors typically utilize constitutive regulatory elements which are responsive to endogenous transcription factors.

Another suitable approach for the delivery of the inhibitors of the present invention, including the inhibitory nucleic acid molecules, the nucleic acid molecules encoding an inhibitory MMP-23 peptide or the inhibitory peptide itself, and the nucleic acid molecules encoding the MMP-23 antibody or the antibodies themselves, involves the use of liposome delivery vehicles.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated inhibitor at the primary target site. This can be accomplished, for example, in a passive manner where the liposome bilayer degrades over time through the action of various agents in the body.

In contrast to passive drug release, active drug release using liposome delivery vehicles can also be achieved. For example, liposome membranes can be constructed to be pH sensitive (see e.g., Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987), which is hereby incorporated by reference in its entirety). When liposomes are endocytosed by a target cell, for example, they can be routed to acidic endosomes which will destabilize the liposome and result in drug release. Alternatively, the liposome membrane can be chemically modified such that an enzyme placed as a coating on the membrane slowly destabilizes the liposome.

Different types of liposomes can be prepared using methods known in the art, see e.g., Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

Yet another approach for delivery of an inhibitory MMP-23 peptide involves the conjugation of the desired peptide or polypeptide to a stabilized polymer to avoid enzymatic degradation of the inhibitory peptide. Conjugated peptides or polypeptides of this type are described in U.S. Pat. No. 5,681,811 to Ekwuribe, which is hereby incorporated by reference in its entirety.

The inhibitors of the present invention can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, intranasal drops). Typically, parenteral administration is the preferred mode of administration.

Inhibitors of the present invention are formulated in accordance with their mode of administration. For oral administration, for example, the inhibitors of the present invention are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the inhibitors or other treatment agents of the present invention. These may be chemically modified so that oral delivery is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, "Soluble Polymer-Enzyme Adducts," In: Enzymes as Drugs, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucrulose, or saccharin. When the dosage unit form is a capsule, it may contain, in addition to materials of the above type, a liquid carrier such as a fatty oil.

The inhibitors of the present invention may also be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver treatment agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of treatment agents can also be achieved using infusion pump devices such as those described by Medtronic (Northridge, Calif.). Such devices allow continuous infusion of desired compounds avoiding multiple injections and multiple manipulations.

In addition to the formulations described previously, treatment agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the inhibitors of the present invention vary depending upon many different factors, including type and stage of cancer or tumor, mode of administration, target site, physiological state of the patient, other medications or therapies administered, and physical state of the patient relative to other medical complications. Treatment dosages need to be titrated to optimize safety and efficacy.

The MMP-23 inhibitors of the present invention can be administered in a single dose or multiple doses. The dosage can be determined by methods known in the art and can be dependent, for example, upon the subject's age, sensitivity, tolerance and overall well-being. Suitable dosages for antibodies can be from about 0.1 mg/kg body weight to about 10.0 mg/kg body weight per treatment.

The inhibitors of the present invention can be administered to an individual (e.g., a human) alone or in conjunction with one or more treatment agents. Accordingly, the subject treatment may be performed in combination with any other anti-cancer treatment. In one embodiment, the MMP-23 inhibitor is administered with an anti-cancer agent, an anti-metastatic agent, or combinations thereof.

In one embodiment, the anti-cancer agent is immunotherapeutic anti-cancer agent. Examples of immunotherapies or immunotherapeutic anti-cancer agents suitable for use in accordance with the present invention include administration of cytokines that stimulate antigen presenting cells, e.g. granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), etc. Additional proteins and/or cytokines known to enhance T cell proliferation and secretion, such as IL-1, IL-2, B7, anti-CD3 and anti-CD28 can be employed simultaneously or sequentially with the MMP-23 inhibitor to augment the immune response. The subject therapy may be combined with the transfection of tumor cells or tumor-infiltrating lymphocytes with genes encoding for various cytokines or cell surface receptors (see Ogasawara et al., "Enhanced Expression of HLA Molecules and Stimulation of Autologous Human Tumor Infiltrating Lymphocytes Following Transduction of Melanoma Cells with Gamma IFN Genes," *Cancer Res.* 53:3561-8 (1993) and Townsend et al. "Tumor Rejection After Direct Costimulation of CD8+ T Cells by B7-Transfected Melanoma Cells," *Science* 259:368-370 (1993), which are hereby incorporated by reference in their entirety. For example, it has been shown that transfection of tumor cells with cDNA encoding CD80 leads to rejection of transfected tumor cells, and can induce immunity to a subsequent challenge by the non-transfected parent tumor cells. The therapeutic according to the present invention enhances this effect.

In another aspect of the present invention, the MMP-23 inhibitor of the present invention may be combined with adoptive T-cell therapy. In one embodiment, tumor-specific host T cells may be combined ex vivo with the subject MMP-23 inhibitor, and tumor antigens or cells, and reinfused into the subject. When administered to a host, the stimulated cells induce a tumoricidal reaction resulting in tumor regression. The host cells may be isolated from a variety of sources, such as lymph nodes, e.g. inguinal, mesenteric, superficial distal auxiliary, etc.; bone marrow; spleen; or peripheral blood, as well as from the tumor, e.g. tumor infiltrating lymphocytes. The cells may be allogeneic or, preferably, autologous. For ex vivo stimulation, the host cells are aseptically removed, and are suspended in any suitable media, as known in the art. The cells are stimulated by any of a variety of protocols, particularly combinations of anti-CD3, B7, anti-CD28, etc., in combination with the MMP-23 inhibitor according to the present invention. The stimulated cells are reintroduced to the host by injection, e.g. intravenous, intraperitoneal, etc. in a variety of pharmaceutical formulations, including such additives as binder, fillers, carriers, preservatives, stabilizing agents, emulsifiers, and buffers. Suitable diluents and excipients are water, saline, glucose, and the like.

Yet another aspect of the present invention relates to a method of identifying a subject as a candidate for adoptive T-cell therapy using T-cells that primarily express KCa3.1 channels. This method involves providing a tumor cell from a subject with a tumor; measuring the expression level of MMP-23 by the tumor cell; comparing, based on the measuring, the expression level of MMP-23 with a control or standard value; and identifying the subject as a candidate for adoptive T-cell therapy using T-cells that primarily express KCa3.1 channels, wherein, based on said comparing, the tumor cell has a higher MMP-23 expression level compared to the control or standard value.

In one embodiment, measuring the expression level of MMP-23 includes contacting the tumor cell with a reagent suitable for detecting the level of MMP-23 expression by the cell and measuring the expression level of MMP-23 by the tumor cell based on the contacting. Suitable reagents and methods of measuring MMP-23 expression are described herein.

This aspect of the present invention relates to selection of T-cells that are not susceptible to inhibition of their Kv1.3 channels by MMP-23 to improve outcomes in tumor immunotherapy. Adoptive T-cell therapies using $T_{CM}$ cells that primarily express KCa3.1 (which is not affected by MMP-23 blockade) (Rangaraju et al., "Kv1.3 Potassium Channels as a Therapeutic Target in Multiple Sclerosis," *Expert Opin. Ther. Targets* 13:909-24 (2009), which is hereby incorporated by reference in its entirety), for example, would be more effective in subjects with high MMP-23 expression in the primary melanoma. Recent adoptive T-cell transfer studies in both mice and humans have shown that $T_{CM}$ mediate more effective tumor rejection (Davey et al., "Preselection Thymocytes are More Sensitive to T Cell Receptor Stimulation Than Mature T Cells," *J. Exp. Med.* 188:1867-74 (1998); Lucas et al., "Divergent Changes in the Sensitivity of Maturing T Cells to Structurally Related Ligands Underlies Formation of a Useful T Cell Repertoire," *Immunity* 10:367-76 (1999); Gattinoni et al., "Acquisition of Full Effector Function in Vitro Paradoxically Impairs the in Vivo Antitumor Efficacy of Adoptively Transferred CD8+ T Cells," *J. Clin. Invest.* 115:1616-26 (2005); Robbins et al., "Cutting Edge: Persistence of Transferred Lymphocyte Clonotypes Correlates with Cancer Regression in Patients Receiving Cell Transfer Therapy," *J. Immunol.* 173:7125-30 (2004); Huang et al., "Survival, Persistence, and Progressive Differentiation of Adoptively Transferred Tumor-Reactive T Cells Associated With Tumor Regression," *J. Immunother.* 28:258-67 (2005); Zhou et al., "Telomere Length of Transferred Lymphocytes Correlates With in Vivo Persistence and Tumor Regression in Melanoma Patients Receiving Cell Transfer Therapy," *J. Immunol.* 175:7046-52 (2005), which are hereby incorporated by reference in their entirety) and selection of such subsets could improve clinical outcomes in subjects.

Thus, in one embodiment, the T-cells that primarily express KCa3.1 channels are central memory T-cells ("$T_{CM}$") expressing KCa3.1 potassium channels, as opposed to effector memory T-cells predominantly expressing Kv1.3 channels (Rangaraju et al., "Kv1.3 Potassium Channels as a Therapeutic Target in Multiple Sclerosis," *Expert Opin. Ther. Targets* 13:909-924 (2009), which is hereby incorporated by reference in its entirety).

Yet a further aspect of the present invention relates to a method of treating a subject having melanoma. This method involves selecting a subject having melanoma and administering an MMP-23 inhibitor to the subject under conditions effective to treat melanoma in the subject.

In one embodiment, the subject has already undergone cancer-related immunotherapy.

The MMP-23 inhibitor according to the present invention is also suitable for administration as an adjuvant. Accordingly, in one embodiment, the MMP-23 is administered as an adjuvant. Adjuvants potentiate the immune response to an antigen. The MMP-23 inhibitors are used as an adjuvant to increase the activation of T cells, and to increase the class switching of antibody producing cells, thereby increasing the concentration of IgG class antibodies produced in response to the immunogen. In one embodiment, the inhibitors are combined with an immunogen in a physiologically acceptable medium, in accordance with conventional techniques for employing adjuvants. The immunogen may be combined in a single formulation with the inhibitor, or may be administered separately. Immunogens include polysaccharides, proteins, protein fragments, haptens, etc. Of particular interest is the use with peptide immunogens. Peptide immunogens may include tumor antigens, e.g., melanoma tumor antigens, that will be known to those of skill in the art.

EXAMPLES

The following examples are provided to illustrate embodiments of the present invention but are by no means intended to limit its scope.

Materials and Methods for Examples 1 to 6

Study Population

Primary melanoma tissues obtained before the start of immunotherapy were retrieved from patients enrolled in the Interdisciplinary Melanoma Cooperative Group, a prospectively collected clinicopathologic-biospecimen database at New York University (NYU) Medical Center (IRB#10362) (Wich et al., "Developing a Multidisciplinary Prospective Melanoma Biospecimen Repository to Advance Translational Research," *Am. J. Trans'. Res.* 1:35-43 (2009), which is hereby incorporated by reference in its entirety), between August 2002 and December 2008. Patients were treated with immune-based therapeutics after primary resection, at recurrence, or in both settings. Immunotherapies were categorized as immune biologics (IFN-α, IL-2, GM-CSF), vaccines (dendritic cell-, peptide-), or anti-CTLA-4 antibodies (ipilimumab, ticilimumab). Informed consent was obtained from all patients at the time of enrollment. Demographic and clinicopathologic information collected included age at pathological diagnosis, gender, primary tumor thickness (mm), ulceration status, mitosis (absent vs. present), histotype, anatomic site, tumor infiltrating lymphocytes (TILs) (absent vs. present: non-brisk, brisk as identified by characteristic lymphocytic morphology on hematoxylin-and-eosin staining) (Clark et al., "Model Predicting Survival in Stage I Melanoma Based on Tumor Progression," *J. Nat'l. Cancer Inst.* 81:1893-904 (1989), which is hereby incorporated by reference in its entirety), recurrence status, and melanoma status at last follow-up (December 2010) (FIG. 1).

Immunohistochemical Analysis

Immunohistochemistry was performed using rabbit polyclonal anti-human MMP-23-carboxyterminal end (ab39087, Abcam, Cambridge, Mass., USA), anti-Kv1.3 (APC-002, Alomone Labs, Ltd., Jerusalem, Israel), and mouse monoclonal anti-human Foxp3 (clone 236A/E7) (eBioscience, San Diego, Calif., USA) on formalin-fixed, paraffin-embedded primary melanoma tissues to detect MMP-23 expression by the melanoma cells, Kv1.3 potassium channel expression on tumor cells and TILs, and the Foxp3+ $T_{regs}$, respectively. An attending pathologist (F.D.) blinded to all clinical data then scored the slides for MMP-23, Foxp3, and Kv1.3 expression. Tumor MMP-23 expression was scored for staining intensity (0=none, 1=faint, 2=intense, 3=very intense) and distribution (0=none, 1=focal (<50%), 2=diffuse (>50%)), which were summed to generate a composite score for each case illustrated in FIGS. 2A-D. For assessment of lymphocyte infiltration, TILs were classified as absent, non-brisk, or brisk. They were defined as brisk when present throughout the vertical growth phase (i.e., large dermal aggregates of melanoma over 15-25 cells wide) or present and infiltrating across the entire base of the vertical growth phase.

Foxp3 expression was scored as the absolute number of positively stained cells with characteristic lymphocytic morphology in a representative high-power field (0.2 mm$^2$) and Kv1.3 expression was scored as the absence or presence of Kv1.3 staining on melanoma cells/TILs. Each representative high-power field was selected by scanning each slide at 100× to identify the field with the highest antibody expression.

In brief, after deparaffinization and rehydration, heat-induced epitope retrieval for MMP-23, Kv1.3, and Foxp3 were performed in 0.01M citrate buffer, pH 6.0, in a 1,200-watt microwave oven at 100% power for 20, 10, and 10 minutes, respectively. Sections were cooled in tap water for 5 minutes, quenched in 0.3% hydrogen peroxide for 30 minutes, washed with PBS, and incubated for 30 minutes with diluted normal blocking serum prepared from goat serum for MMP-23 and horse serum for Foxp3 while a blocking solution containing 5% bovine serum albumin, 0.1% sodium azide, and 5% goat serum was used for Kv1.3. Slides were then incubated with each primary antibody diluted in buffer (MMP-23, 1:100; Kv1.3, 1:50; Foxp3, 1:500) at room temperature for 1 hour and at 4° C. overnight, after which they were washed in buffer and incubated with diluted biotinylated secondary antibodies (goat anti-rabbit at 1:500 for both MMP-23 and Kv1.3-stained sections; horse anti-mouse at 1:500 for Foxp3-stained sections, Vector Laboratories, Burlingame, Calif., USA) for 1 hour. Avidin-biotinylated horseradish peroxidase complexes diluted at 1:500 (ABC reagent, Vector Laboratories) were added. MMP-23 and Kv1.3 staining were both visualized with peroxidase (ImmPACT™ NovaRED™ Peroxidase Substrate, Vector Laboratories) and diaminobenzidine (DAB substrate kit, Vector Laboratories) was used to visualize Foxp3 staining Sections were washed in distilled water, counterstained with hematoxylin, dehydrated, and then mounted with permanent media. Appropriate positive and negative controls were included with study sections as well.

Isolation of Lymphocytes from Fresh Tissue for Flow Cytometry

Lymphocytes were isolated from fresh tissue lymph node specimens of melanoma patients undergoing metastasectomy as previously described (Santin et al., "Induction of Tumor-specific Cytotoxicity in Tumor Infiltrating Lymphocytes by HPV16 and HPV18 E7-pulsed Autologous Dendritic Cells in Patients with Cancer of the Uterine Cervix," *Gynecol. Oncol.* 89:271-80 (2003), which is hereby incorporated by reference in its entirety). In brief, fresh tissues were mechanically minced in complete RPMI (Life Technologies, Grand Island, N.Y., USA) to portions no larger than 1-3 mm$^3$, washed twice in RPMI, resuspended in RPMI containing 0.14% collagenase type I (Sigma-Aldrich, St. Louis, Mo., USA) and 0.01% DNAse (Sigma-Aldrich), and then incubated overnight at 4° C. with constant mixing. A single-cell suspension was obtained by passing the solution through a 75 μm-mesh, which was then washed twice in RPMI and resuspended at 2×10$^6$ cells/mL. After an overnight incubation in T75 flasks at 37° C., the non-adherent lymphocytes were collected.

Assessment of Isolated T-cell Kv1.3 Expression and Activation by CD69 Upregulation Isolated lymphocytes were suspended at 10$^6$ cells/mL in complete RPMI in 24-well plates and activated by the addition of 5 μg/mL Concanavalin A (Sigma-Aldrich). After an overnight culture at 37° C., activated and unactivated cells were assessed for expression of Kv1.3 and upregulation of CD69. For Kv1.3 expression, unactivated cells were stained with FITC-anti-Kv1.3 (1:20) (Alomone Labs, Ltd., Jerusalem, Israel), APC-anti-CD8 (1:50) (HIT8a, BioLegend, San Diego, Calif., USA), PE-anti-CD4 (1:50) (OKT-4, eBioscience, San Diego, Calif., USA), and Pacific Blue-anti-CCR7 (1:50) (G043H7, eBioscience) in PBS+1% FBS (Fisher Scientific, Pittsburgh, Pa., USA) for 30 minutes at room temperature. Samples were also independently stained with FITC rabbit IgG isotype control (1:50) (eBioscience). For CD69 expression, activated and unactivated cells were stained with PE-anti-CD69 (1:50) (FN50, BioLegend), APC-anti-CD8 (1:50), FITC-anti-CD4 (1:50) (SK3, BioLegend), and Pacific Blue-anti-CCR7 (1:50). Samples were then washed twice and evaluated by flow cytometry using the LSR II flow cytometer (BD Biosciences). All data were analyzed using FlowJo flow cytometry analysis software (TreeStar, Inc.). Kv1.3 expression is presented as the mean fluorescence intensity (MFI) above isotype control MFI, determined as (sample MFI−isotype MFI)/(isotype MFI). CD69 upregulation is similarly presented as (activated sample MFI)/(unactivated sample MFI).

FACS Analysis

Fresh whole blood was collected from a subset of patients and directly labeled by incubation for 30 minutes with FITC-conjugated anti-Kv1.3 (APC-101-F, Alomone Labs, Ltd.), Pacific Blue™-conjugated anti-CD4 (clone OKT4) (BioLegend, San Diego, Calif., USA), and APC-conjugated anti-CD8a (clone HIT8a) (BioLegend) in FACS buffer (5% fetal bovine serum in phosphate-buffered saline, pH 7.4). Samples were washed twice, fixed with 4% paraformaldehyde for 15 minutes at room temperature, washed twice more and resuspended in FACS buffer for analysis. All data were collected on a LSR II flow cytometer (BD Biosciences) and analyzed using FlowJo flow cytometry analysis software.

Statistical Analysis

Descriptive statistics were calculated for MMP-23 expression, T-cell Kv1.3 expression, and clinicopathologic variables. Univariate associations between MMP-23 expression and continuous clinicopathologic variables were assessed by the ANOVA test or Kruskal-Wallis test, as appropriate. Univariate associations between MMP-23 expression and categorical clinicopathologic variables (including recurrence) were assessed by the chi-square test or Fisher's exact test, as appropriate. Categories of high and low MMP-23 expression were explored in various analyses. The correlation between primary melanoma MMP-23 expression and peripheral T-cell Kv1.3 expression was assessed by the Spearman-rank correlation coefficient. All p-values are two-sided with statistical significance evaluated at the 0.05 alpha level. All analyses were performed in SPSS Version 21.0 (SPSS Inc., Chicago, Ill.).

Example 1—Patient Selection and Treatment

FIG. 3 illustrates the primary tumor characteristics and clinicopathological factors of the cohort of melanoma patients studied. Primary melanoma specimens acquired prior to the initiation of immunotherapy were examined for the 85 cases. Immunotherapy was given in one of three settings: (i) after primary resection (n=37), (ii) at recurrence (n=42), or (iii) after primary resection and at recurrence (n=6) (FIG. 3). Median follow-up time from the date of pathological diagnosis was 4.9 years (range: 0.7-15.6 years) for the whole cohort and 5.8 years (range: 1.4-15.0 years) for survivors. Melanoma was the cause of death for 41/42 patients who died during follow-up.

Example 2—Increased Primary Melanoma MMP-23 Expression is Associated with Resistance to Immunotherapy in Patients Treated with Immune Biologics To evaluate the potential role of MMP-23 in tumor immune escape, the relationship between tumor MMP-23 expression, as measured by a composite score of MMP-23 staining intensity and distribution, and immunotherapy outcomes, as measured by the rate of recurrence was evaluated. Of the patients treated, 41/85 (48.2%) received either vaccines (n=22) or immune biologics (n=19) immunotherapy as primary adjuvant treatment. Considering those receiving vaccines and immune biologics combined, recurrence was detected in 5/12 (41%) of patients with low MMP-23 expression (defined as composite score=0-2) compared to 23/29 (79%) of patients with high MMP-23 expression (defined as composite score=>3) (P=0.03). However, because vaccines and immune biologics target CD8+CCR7+(Tcm) and CD8+CCRY−(Tem) T-cell subsets, respectively, their outcomes were considered separately to determine if the observed relationship between MMP-23 expression and recurrence could be attributed to an effect on a specific T-cell subset (FIG. 4). Considering only patients receiving vaccine therapy, no significant difference in recurrence was detected between patients with low MMP-23 expression (5/8, 63%) and patients with high MMP-23 expression (10/14, 71%) (P=0.99). However, considering patients receiving immune biologics, higher MMP-23 expression was associated with an increased risk of recurrence, as recurrence was detected in 0/4 patients with low MMP-23 expression compared to 13/15 (87%) in patients with high MMP-23 expression (P=0.004) (FIG. 4). These results show that MMP-23 specifically affects Tem cells, as immune biologic adjuvants including IFN-α, IL-2, and GM-CSF function by targeting Tem expansion.

Example 3—Higher Melanoma MMP-23 Expression is Associated with a Blunted Intrinsic Anti-tumor Response MMP-23 can inhibit T-cell activation by blocking Kv1.3 channels, thereby reducing activation-induced proliferation and motility (Feske, "Calcium Signalling in Lymphocyte Activation and Disease," *Nat. Rev. Immunol.* 7:690-702 (2007); Matheu et al., "Imaging of Effector Memory T Cells During a Delayed-Type Hypersensitivity Reaction and Suppression by Kv1.3 Channel Block," *Immunity* 29(4):602-14 (2008), which is hereby incorporated by reference in its entirety). Furthermore, prolonged inhibition of Kv1.3 can prevent Tem cells from receiving activation or survival signals, resulting in death due to cytokine deprivation (Rangaraju et al., "Kv1.3 Potassium Channels as a Therapeutic Target in Multiple Sclerosis," *Expert Opin. Ther. Targets* 13:909-24 (2009), which is hereby incorporated by reference in its entirety). It was therefore considered that the observed increased recurrence rate in patients with high MMP-23 expression in response to immunotherapies incorporating immune biologic adjuvants could be due to inhibition of the intrinsic anti-tumor response. The relationship between primary melanoma MMP-23 expression and anti-tumor immunity was evaluated by determining the presence and degree of infiltration of TILs, which provide measures for the strength of intrinsic anti-tumor immune response (Clark et al., "Model Predicting Survival in Stage I Melanoma Based on Tumor Progression," *J. Nat'l. Cancer Inst.* 81:1893-904 (1989); Clemente et al., "Prognostic Value of Tumor Infiltrating Lymphocytes in the Vertical Growth Phase of Primary Cutaneous Melanoma," *Cancer* 77:1303-10 (1996), which are hereby incorporated by reference in their entirety) (FIGS. 5A-D). It was observed that increased melanoma MMP-23 expression was found to be inversely associated with the presence of TILs (presence of TILs=79.4% vs. 53.8% for underexpressed and overexpressed MMP23, respectively, P=0.05). Further, quantification of the intensity of lymphocytic infiltration showed a significant inverse correlation between MMP-23 expression and brisk lymphocyte infiltration (brisk TILs=65.0% vs. 25.0% for underexpressed and overexpressed MMP23, respectively, P=0.04). These results suggest a role for tumor MMP-23 in the suppression of the intrinsic anti-tumor response.

In addition to tumor-specific T-lymphocytes, the TIL population is also comprised of immunosuppressive Foxp3+ regulatory T-cells ($T_{regs}$) that play an important role in immune evasion (Oble et al., "Focus on TILs: Prognostic Significance of Tumor Infiltrating Lymphocytes in Human Melanoma," *Cancer Immun.* 9:3 (2009); De Panfilis et al., "Phase- and Stage-Related Proportions of T Cells Bearing the Transcription Factor FOXP3 Infiltrate Primary Melanoma," *J. Invest. Dermatol.* 128:676-84 (2008), which are hereby incorporated by reference in their entirety). The accumulation of $T_{regs}$ in the tumor microenvironment could be attributed to a number of factors, including local expression and secretion of factors affecting $T_{reg}$ migration and retention, expansion of naturally occurring $T_{regs}$, or de novo generation of induced $T_{regs}$ (Jacobs et al., "Regulatory T Cells in Melanoma: The Final Hurdle Towards Effective Immunotherapy?" *Lancet Oncol.* 13(1):e32-42 (2012), which is hereby incorporated by reference in its entirety). To investigate the potential role of melanoma MMP-23 in contributing to conditions favorable to tumor $T_{regs}$, the relationship between MMP-23 expression and $T_{reg}$ prevalence was assessed, as determined by the number of Foxp3 positive cells. A trend was observed towards an increased average number of $T_{regs}$ in primary melanomas with higher MMP-23 expression (53.1±33.8 vs. 35.0±25.1 for overexpressed and underexpressed MMP23, respectively, P=0.07) (FIGS. 6A-D). Together these results indicate a role of MMP-23 expression overexpression in blunting the intrinsic immune response to melanoma as it affects the prevalence, distribution, and composition of TILs in favor of tumor evasion of anti-tumor response.

Example 4—In Vitro Assessment of MMP-23 Inhibition of Tem Activation

Figures 7A, 7B:
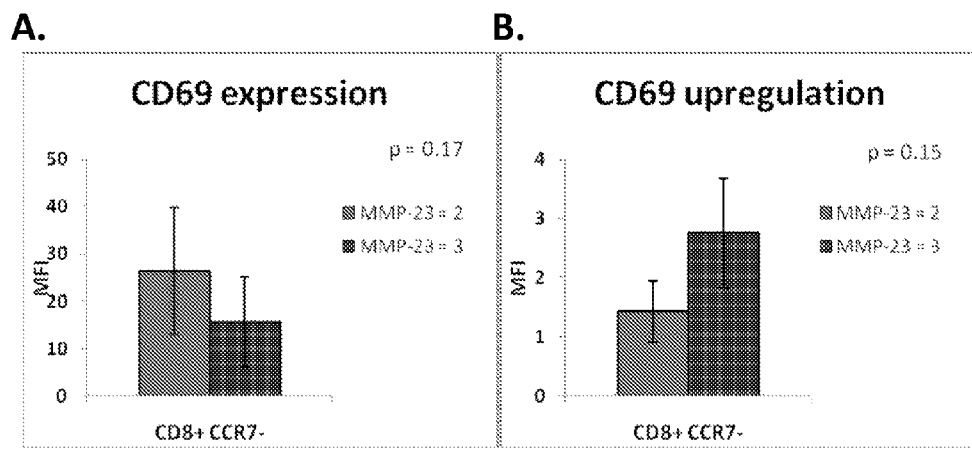
FIGS. 7A-B are graphs showing T-cell CD69 expression in fresh tissue specimens of melanoma patients.

To more specifically investigate the role of MMP-23 in inhibition of Tem activation, lymphocytes were isolated from fresh tissue lymph node specimens with low or high MMP-23 expression to evaluate and compare Tem and Tcm populations (FIGS. 7A-B). These fresh tissues were collected from a separate cohort of immunotherapy-naïve melanoma patients undergoing metastasectomy. The isolated T-cells were stained for CCR7 to discriminate between Tcm and Tem populations (Sallusto et al., "Two Subsets of Memory T Lymphocytes With Distinct Homing Potentials and Effector Functions," *Nature* 401(6754):708-12 (1999), which is hereby incorporated by reference in its entirety) and probed for expression of CD69, a marker for T cell activation whose upregulation indicates recent activation, detectable for up to 72 hours following activation (Testi et al., "Leu 23 Induction as an Early Marker of Functional CD3/T Cell Antigen Receptor Triggering. Requirement for Receptor Cross-Linking, Prolonged Elevation of Intracellular (Ca++) and Stimulation of Protein Kinase C," *J. Immunol.* 142(6):1854-60 (1989), which is hereby incorporated by reference in its entirety). The data shows that in CD8+ CCR7− T cells (Tem), which express significantly higher levels of Kv1.3 compared to CCR7+(Tcm) cells (Rangaraju et al., "Kv1.3 Potassium Channels as a Therapeutic Target in Multiple Sclerosis," *Expert Opin. Ther. Targets* 13:909-24 (2009), which are hereby incorporated by reference in their entirety) and are dependent on Kv1.3 for robust activation, CD69 expression tended to be higher in samples from patients with lower MMP-23 expression (P=0.17) (FIGS. 7A-B), although the available sample size likely limited the statistical power of the analysis. This suggests that increased melanoma MMP-23 expression contributes in part to the reduced activation of Kv1.3-dependent T-cells.

To confirm that the decreased level of activation of Tem cells was due to in vivo inhibition, the isolated Tem cells were activated in vitro and again assessed their degree of CD69 upregulation (FIGS. 8A-B). Tem cells from patients with higher MMP-23 expression tended to show greater CD69 upregulation (P=0.15) (FIGS. 7A-B), indicating that, upon removal from presumptive inhibitory in vivo conditions, these cells were indeed capable of robust activation. While Tem cells from patients with low MMP-23 showed a smaller increase in CD69 upregulation after in vitro activation, this was likely due to the fact that they were already expressing higher levels of CD69 due to in vivo activation. Combined, these data indicate that while Tem cells retain the ability to become activated, in vivo activation may be limited by MMP-23 expression, and MMP-23 expression blunts the intrinsic anti-tumor response through inhibition of Tem function.

Figure 9:
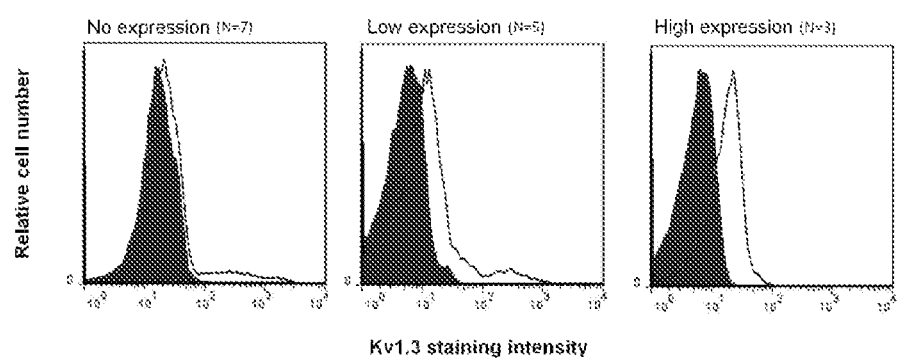
FIG. 9 shows post-immunotherapy peripheral T-cell Kv1.3 expression using FACS plots of peripheral CD4+/CD8+ T-cells analyzed by flow cytometry using a Kv1.3-specific antibody.

Example 5—Peripheral T-Cell Kv1.3 Expression is not Predictive of Primary Melanoma MMP-23 Expression It was postulated that secreted MMP-23 can also modulate surface expression of Kv1.3 on T-cells such that MMP-23's effect on peripheral T-cells may serve as a potential predictor for the systemic anti-tumor response following immunotherapy. As a proof of principal, the possible relationship between MMP-23 expression in pre-immunotherapeutic primary tissues and the systemic anti-tumor immune response following immunotherapy was investigated. Fresh whole blood was acquired from a subset of patients (n=15) for post-immunotherapy surface expression analysis of Kv1.3 expression on peripheral T-cells by flow cytometry (FIG. 9). MMP-23 was expressed in 13/15 primary tumors, and a weak positive correlation between primary melanoma MMP-23 composite score and both peripheral blood CD4+ and CD8+ T-cell Kv1.3 expression was observed (spearman r=0.21, P=0.49). These data show that MMP23 expression in the tumor tissue is predictive of the response to immunotherapy at least in a subset of patients.

Example 6—Effect of MMP-23 on Tumor Kv1.3 Expression

Tumor-derived MMPs in melanoma and other cancers can mediate microenvironmental changes regulating cancer progression (Hofmann et al., "Matrix Metalloproteinases in Human Melanoma," *J. Invest. Dermatol.* 115:337-44 (2000); Egeblad & Werb, "New Functions for the Matrix Metalloproteinases in Cancer Progression," *Nat. Rev. Cancer* 2:161-74 (2002); Roy et al., "Matrix Metalloproteinases as Novel Biomarkers and Potential Therapeutic Targets in Human Cancer," *J. Clin. Oncol.* 27:5287-97 (2009), which are hereby incorporated by reference in their entirety).

Melanoma cells also express Kv1.3 themselves (Artym & Petty, "Molecular Proximity of Kv1.3 Voltage-Gated Potassium Channels and Beta(1)-Integrins on the Plasma Membrane of Melanoma Cells: Effects of Cell Adherence and Channel Blockers," *J. Gen. Physiol.* 120:29-37 (2002), which is hereby incorporated by reference in its entirety), although the role of tumor Kv1.3 expression is unclear. However, blockade of melanoma Kv1.3 has been shown to dysregulate integrin function, affecting cell adherence (Artym & Petty, "Molecular Proximity of Kv1.3 Voltage-Gated Potassium Channels and Beta(1)-Integrins on the Plasma Membrane of Melanoma Cells: Effects of Cell Adherence and Channel Blockers," *J. Gen. Physiol.* 120:29-37 (2002), which is hereby incorporated by reference in its entirety). Further, in prostate cancer, reduced Kv1.3 expression was associated with poor clinical outcome (Abdul & Hoosein, "Reduced Kv1.3 Potassium Channel Expression in Human Prostate Cancer," *J. Membr. Biol.* 214:99-102 (2006), which is hereby incorporated by reference in its entirety). It was hypothesized that secreted melanoma MMP-23 may, therefore, influence outcomes through inhibition of Kv1.3 channels on melanoma cells as well as T-cells. Melanoma Kv1.3 surface expression may be inhibited by in cis MMP-23 trapping of Kv1.3 at the endoplasmic reticulum (Rangaraju et al., "Potassium Channel Modulation by a Toxin Domain in Matrix Metalloprotease 23," *J. Biol. Chem.* 285:9124-36 (2010), which is hereby incorporated by reference in its entirety). To examine the possible effect of melanoma MMP-23 expression on tumor expression of Kv1.3, 20 primary melanomas were evaluated for both MMP-23 and Kv1.3 expression. Kv1.3 expression was absent on 10/15 (67%) primary tumors that had high MMP-23 expression. However, Kv1.3 expression was also absent on 5/5 (100%) tumors that had absent or low MMP-23 expression (P=0.27). These data suggest that MMP-23 is not a sole indicator of tumor Kv1.3 expression. Kv1.3 was observed to be expressed in tumors with high MMP-23, but also absent in tumors with low MMP-23 expression. Further, considering the recurrence rates following immunotherapy, recurrence was observed in 11/15 (73%) of patients absent of tumor Kv1.3 staining and observed in 4/5 (80%) of patients with positive Kv1.3 staining (P=0.99), suggesting no link between tumor Kv1.3 and clinical outcome. Together, these data suggest that tumor MMP-23 does not directly affect tumor Kv1.3 expression via an in cis mechanism, and that tumor Kv1.3 expression is not linked to the rate of recurrence following immune therapies, further supporting an in trans mechanism for MMP-23 affecting immunotherapy outcomes by inhibition of T-cell activation and function.

Discussion of Examples 1-6

This is the first study to examine the expression of MMP-23 in melanoma and the data show that it represents a novel tumor-induced immune escape mechanism (Schreiber et al., "Cancer Immunoediting: Integrating Immunity's Roles in Cancer Suppression and Promotion," *Science* 331:1565-70 (2011), which is hereby incorporated by reference in its entirety) and immune checkpoint blockade target (Weber, "Immune Checkpoint Proteins: A New Therapeutic Paradigm for Cancer—Preclinical Background:

CTLA-4 and PD-1 Blockade," *Semin. Oncol.* 37:430-9 (2010), which is hereby incorporated by reference in its entirety). Structural similarities between MMP-23(TxD) and the T-cell potassium channel inhibitor toxins BgK and ShK (Rangaraju et al., "Potassium Channel Modulation by a Toxin Domain in Matrix Metalloprotease 23," *J. Biol. Chem.* 285:9124-36 (2010), which is hereby incorporated by reference in its entirety) provide the rationale for studying MMP-23 as a potential immunomodulator during melanoma progression. MMP-23(TxD) selectively blocks the voltage-gated potassium channel Kv1.3 that maintains the membrane potential required for sustained T-cell activation (Rangaraju et al., "Potassium Channel Modulation by a Toxin Domain in Matrix Metalloprotease 23," *J. Biol. Chem.* 285:9124-36 (2010), which is hereby incorporated by reference in its entirety). These data indicate that melanoma MMP-23 expression diminishes the anti-tumor T-cell response, and that it acts in trans by blocking Kv1.3 and suppressing T-cell activation. With respect to how MMP-23 expression affects the composition of the infiltrating T-cells, it is shown that increased MMP-23 correlates with higher number of $T_{reg}$ infiltrates. Finally, Kv1.3 expression and function on tumor cells can also play an important role in clinical outcomes (Abdul & Hoosein, "Reduced Kv1.3 Potassium Channel Expression in Human Prostate Cancer," *J. Membr. Biol.* 214:99-102 (2006), which is hereby incorporated by reference in its entirety), and intracellular trapping of Kv1.3, along with blocking of functional Kv1.3 expressed on melanoma cells, was considered as a possible additional role for melanoma MMP-23. However, the data suggest that there is no relationship between tumor MMP-23 expression and tumor Kv1.3 expression. Combined, these data indicate a role for tumor MMP-23 in modulating the infiltration and activation of tumor-reactive lymphocytes, as indicated by the higher rate of recurrence for patients with high MMP-23-expressing primary melanomas treated with immune biologics.

Anti-tumor T-cells comprise the majority of the tumor lymphocytic infiltrate, and it is shown that the number, intensity of infiltration, and composition of TILs are negatively affected by melanoma MMP-23 expression. Increased tumor expression of MMP-23, therefore, mediates intrinsic tolerance with the potential to confer resistance against immunotherapy. As such, an evaluation of melanoma MMP-23 expression is particularly useful in selecting candidates for adoptive T-cell therapy, the success of which depends on the harvest, expansion and immunophenotype of TILs (June, "Adoptive T Cell Therapy for Cancer in the Clinic," *J. Clin. Invest.* 117:1466-76 (2007), which is hereby incorporated by reference in its entirety). Furthermore, the results indicate a clinical relevance of assessing primary melanoma MMP-23 expression prior to initiating adjuvant treatment with immune biologics. Melanoma MMP-23 expression negatively correlates with response to adjuvant immune biologic therapy, which is consistent with both the hypothesis and the mechanism of action of immune biologics. Immune biologics, such as IFN-α, IL-2, and GM-CSF, preferentially expand Tem cells, which, when activated, express an increased number of Kv1.3 channels (Sikora et al., "IFN-Alpha Enhances Peptide Vaccine-Induced CD8+ T Cell Numbers, Effector Function, and Antitumor Activity," *J. Immunol.* 182:7398-407 (2009); Klebanoff et al., "Central Memory Self/Tumor-Reactive CD8+ T Cells Confer Superior Antitumor Immunity Compared With Effector Memory T Cells," *Proc. Nat'l. Acad. Sci. U.S.A.* 102:9571-6 (2005); Hueman et al., "Analysis of Naïve and Memory CD4 and CD8 T Cell Populations in Breast Cancer Patients Receiving a HER2/Neu Peptide (E75) and GM-CSF Vaccine," *Cancer Immunol. Immunother.* 56:135-46 (2007), which are hereby incorporated by reference in their entirety). Vaccines, in contrast, induce the central memory T-cell subset that is characterized by low Kv1.3 expression, and are not dependent on Kv1.3 function for activation (Rangaraju et al., "Kv1.3 Potassium Channels as a Therapeutic Target in Multiple Sclerosis," *Expert Opin. Ther. Targets* 13:909-24 (2009); Butler et al., "Immunologic Considerations for Generating Memory CD8 T Cells Through Vaccination," *Cell Microbiol.* 13:925-33 (2011), which are hereby incorporated by reference in their entirety). This could explain the lack of an observed association between melanoma MMP-23 expression and recurrence among patients treated with adjuvant vaccine therapy. CTLA-4 blockade also promotes a central memory T-cell response (Rudolph et al., "Blockade of CTLA-4 Decreases the Generation of Multifunctional Memory CD4+ T Cells In Vivo," *J. Immunol.* 186:5580-9 (2011), which is hereby incorporated by reference in its entirety), which points to the limited clinical utility of evaluating tumor MMP-23 expression before starting anti-CTLA-4 therapy. However, there were too few cases in this study to examine the possible association between primary melanoma MMP-23 expression and recurrence with this type of treatment.

Inhibition of MMP-23 in combination with other immunotherapies may further augment anti-tumor immunity. With the clinical success of monoclonal antibodies against other inhibitory immune checkpoint proteins in melanoma, including CTLA-4 (Hodi et al., "Improved Survival With Ipilimumab in Patients With Metastatic Melanoma," *N. Engl. J. Med.* 363:711-23 (2010); Robert et al., "Ipilimumab Plus Dacarbazine for Previously Untreated Metastatic Melanoma," *N. Engl. J. Med.* 364:2517-26 (2011); Peggs et al., "Blockade of CTLA-4 on Both Effector and Regulatory T Cell Compartments Contributes to the Antitumor Activity of Anti-CTLA-4 Antibodies," *J. Exp. Med.* 206:1717-25 (2009), which are hereby incorporated by reference in their entirety) and PD1 (Weber, "Immunotherapy for Melanoma," *Curr. Opin. Oncol.* 23:163-9 (2011), which is hereby incorporated by reference in its entirety), anti-MMP-23 therapy also holds promise as a potential treatment strategy. However, such strategies must consider the possibility of off-target effects and, therefore, the normal tissue distribution and physiologic role of MMP-23 must be understood. Unlike other MMPs, MMP-23 is widely expressed under physiologic conditions, in particular at high levels in the ovary, testis, prostate, and heart and at low levels in the lung, pancreas, and colon (Velasco et al., "Cloning and Characterization of Human MMP-23, a New Matrix Metalloproteinase Predominantly Expressed in Reproductive Tissues and Lacking Conserved Domains in Other Family Members," *J. Biol. Chem.* 274:4570-6 (1999); Pei et al., "Cysteine Array Matrix Metalloproteinase (CA-MMP)/MMP-23 is a Type II Transmembrane Matrix Metalloproteinase Regulated by a Single Cleavage for Both Secretion and Activation," *J. Biol. Chem.* 275:33988-97 (2000), which are hereby incorporated by reference in their entirety). Therefore, intralesional delivery of MMP-23 inhibitors may therefore be preferred over systemic injection for minimizing possible off-target effects. Furthermore, locoregional MMP-23 inhibition has the potential to alter both the number and the composition of the TILs, such that adoptive T-cell therapy candidates could benefit from pre-treatment with intralesional MMP-23 inhibitors. Combination therapy with MMP-23 and BRAF inhibitors also warrants further investigation since BRAF inhibitors are immunosensitizing agents (Boni et al., "Selective BRAFV600E Inhibition Enhances T-Cell Recognition of Melanoma Without Affecting Lymphocyte Function," *Cancer Res.* 70:5213-9 (2010), which is hereby incorporated by reference in its entirety) as well. The $^{V600E}$BRAF inhibitor vemurafenib (Chapman et al., "Improved Survival With Vemurafenib in Melanoma With BRAF V600E Mutation," *N. Engl. J. Med.* 364:2507-16 (2011), which is hereby incorporated by reference in its entirety) increases the number of activated T-cells while inhibiting mutant BRAF in melanoma cells, as it paradoxically increases MAPK signaling in cells harboring wild-type BRAF (Poulikakos et al., "RAF Inhibitors Transactivate RAF Dimers and ERK Signalling in Cells With Wild-Type BRAF," *Nature* 464:427-30 (2010), which is hereby incorporated by reference in its entirety).

In identifying MMP-23 as a novel immune checkpoint blockade target, it is important to recognize that inhibition of MMP-23 will likely result in immune-related adverse events, much like the inhibition of CTLA-4 (Hodi et al., "Improved Survival With Ipilimumab in Patients With Metastatic Melanoma," *N. Engl. J. Med.* 363:711-23 (2010), which is hereby incorporated by reference in its entirety). Ongoing efforts to identify biomarkers to both predict and monitor the response to anti-CTLA-4 therapy are under way. As additional studies of the role of MMP-23 in melanoma are warranted, parallel studies to identify those patients most likely to benefit from MMP-23 inhibition are also needed. This study provides support for both as data indicate that an assessment of melanoma MMP-23 expression by routine immunohistochemistry is useful, much like using immunohistochemistry to determine the estrogen/progesterone receptor status in breast cancer. Non-invasive modalities to monitor the clinical efficacy of molecularly targeted therapies, however, have yet to be developed. In this study, the clinical utility of peripheral T-cell Kv1.3 expression was evaluated as a potential biomarker of response to immunotherapy by examining the correlation between primary melanoma MMP-23 expression prior to immunotherapy and peripheral CD4$^+$/CD8$^+$ T-cell Kv1.3 expression after immunotherapy. A positive correlation between primary melanoma MMP-23 composite score was noted with peripheral blood T-cell Kv1.3 expression. Potential confounders in this evaluation include the heterogeneity in the type and the timing of immunotherapy (i.e., adjuvant vs. at recurrence) as well as the presence of infectious/inflammatory co-morbid conditions at the time of peripheral blood analysis, such as type I diabetes mellitus, psoriasis, rheumatoid arthritis, and asthma. The evaluation of Kv1.3 expression by primary TILs is similarly affected by these limitations.

This study also indicates a dual mechanism of action of melanoma MP-23 in tumor progression. While much of this study focused on the potential role of melanoma MMP-23 in blunting anti-tumor immunity via blockade of T-cell Kv1.3 expression, the possibility that melanoma MMP-23 may also act in cis by trapping Kv1.3 in the endoplasmic reticulum and preventing surface expression was also explored. Of the primary melanomas evaluated for Kv1.3 surface expression, most were negative, which may reflect the suppression of the Kv1.3 surface expression due to in cis MMP-23 trapping (Rangaraju et al., "Potassium Channel Modulation by a Toxin Domain in Matrix Metalloprotease 23," *J. Biol. Chem.* 285:9124-36 (2010), which is hereby incorporated by reference in its entirety), or an absence of Kv1.3 expression altogether. Kv1.3 channels on melanoma cells have previously been shown to be in close proximity to 131-integrins, such that blockade of Kv1.3 channels dysregulates integrin function and results in loss of cell adherence (Artym & Petty, "Molecular Proximity of Kv1.3 Voltage-Gated Potassium Channels and Beta(1)-Integrins on the Plasma Membrane of Melanoma Cells: Effects of Cell Adherence and Channel Blockers," *J. Gen. Physiol.* 120:29-37 (2002), which is hereby incorporated by reference in its entirety). Disruption of cell-cell/cell-matrix adhesion is one of many steps in metastatic progression, and evidence from prostate cancer support the association between reduced tumor cell Kv1.3 expression and poor clinical outcome (Abdul & Hoosein, "Reduced Kv1.3 Potassium Channel Expression in Human Prostate Cancer," *J. Membr. Biol.* 214:99-102 (2006), which is hereby incorporated by reference in its entirety). Studies in breast and colon cancer, in contrast, suggest that blockade of tumor cell Kv1.3 expression is protective (Abdul et al., "Activity of Potassium Channel-Blockers in Breast Cancer," *Anticancer Res.* 23:3347-51 (2003); Abdul & Hoosein, "Voltage-Gated Potassium Ion Channels in Colon Cancer," *Oncol. Rep.* 9:961-4 (2002), which are hereby incorporated by reference in their entirety) as it prevents progression through the $G_1$/S checkpoint, which requires transient hyperpolarization (Blackiston et al., "Bioelectric Controls of Cell Proliferation: Ion Channels, Membrane Voltage and the Cell Cycle," *Cell Cycle* 8:3519-28 (2009), which is hereby incorporated by reference in its entirety). Progression through the $G_2$/M checkpoint, however, is associated with depolarization (Blackiston et al., "Bioelectric Controls of Cell Proliferation: Ion Channels, Membrane Voltage and the Cell Cycle," *Cell Cycle* 8:3519-28 (2009), which is hereby incorporated by reference in its entirety). In trapping Kv1.3 in the endoplastic reticulum, melanoma MMP-23 may likewise alter the tumor cell membrane potential and facilitate the transition to the M phase, which appears to be supported by the observed increased prevalence of primary melanomas with higher MMP-23 expression that were found to have mitotic activity.

In summary, the studies described herein are the first to show the role MMPs play in tumor-induced immune escape. Melanoma MMP-23 expression negatively modulates T-cell activation such that it also represents a novel immune checkpoint blockade target. MMP-23 inhibition in combination with other therapeutic agents may be more effective than as monotherapy.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:
1. A method comprising:
providing a sample comprising a tumor cell from a subject having melanoma; and
detecting the expression level of MMP-23 by the tumor cell in the sample by contacting the sample with an anti-MMP-23 antibody and detecting binding between MMP-23 and the anti-MMP-23 antibody.
2. The method according to claim 1 further comprising: administering an MMP-23 inhibitor to the subject.
3. The method according to claim 1, wherein the subject is a human.

* * * * *